(12) United States Patent
Kruse

(10) Patent No.: US 9,421,329 B2
(45) Date of Patent: Aug. 23, 2016

(54) INFUSION DEVICE OCCLUSION DETECTION SYSTEM

(71) Applicant: Tandem Diabetes Care, Inc., San Diego, CA (US)

(72) Inventor: Geoffrey Kruse, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 659 days.

(21) Appl. No.: 13/832,531

(22) Filed: Mar. 15, 2013

(65) Prior Publication Data

US 2014/0276537 A1 Sep. 18, 2014

(51) Int. Cl.
*A61M 5/168* (2006.01)
*A61M 5/145* (2006.01)
*A61M 5/142* (2006.01)

(52) U.S. Cl.
CPC ....... *A61M 5/16854* (2013.01); *A61M 5/1456* (2013.01); *A61M 5/14244* (2013.01); *A61M 2205/33* (2013.01); *A61M 2205/502* (2013.01)

(58) Field of Classification Search
CPC ............... A61M 5/16854; A61M 5/14244; A61M 5/1456; A61M 2205/33; A61M 2205/502; F04B 53/14; F04B 53/144; F04B 49/08; F01B 7/20
USPC .................. 604/111, 500, 218, 311
See application file for complete search history.

(56) References Cited

U.S. PATENT DOCUMENTS

| | | | |
|---|---|---|---|
| 3,985,133 A | 10/1976 | Jenkins et al. | |
| 4,178,938 A | 12/1979 | Au | |
| 4,650,471 A | 3/1987 | Tamari | |
| 4,919,596 A | 4/1990 | Slate et al. | |
| 5,000,739 A | 3/1991 | Kulisz et al. | |
| 5,085,644 A | 2/1992 | Watson et al. | |
| 5,087,245 A | 2/1992 | Doan | |
| 5,103,211 A | 4/1992 | Daoud et al. | |
| 5,131,816 A | 7/1992 | Brown et al. | |
| 5,178,603 A | 1/1993 | Prince | |
| 5,215,450 A | 6/1993 | Tamari | |
| 5,242,408 A | 9/1993 | Jhuboo et al. | |
| 5,247,434 A | 9/1993 | Peterson et al. | |
| 5,273,406 A | 12/1993 | Feygin | |

(Continued)

FOREIGN PATENT DOCUMENTS

| WO | WO 95/32013 | 11/1995 |
|---|---|---|
| WO | WO 01/30422 A1 | 5/2001 |

(Continued)

OTHER PUBLICATIONS

Application and File Wrapper for U.S. Appl. No. 13/829,115 filed Mar. 14, 2013 inventor Rosinko et al., as available on PAIR at www.uspto.gov.

(Continued)

*Primary Examiner* — Theodore Stigell
*Assistant Examiner* — Amber Stiles
(74) *Attorney, Agent, or Firm* — Patterson Thuente Pedersen, P.A.

(57) ABSTRACT

Device and method embodiments are described which are capable of detecting and alerting a user of an infusion device to a hindrance in the ability to deliver measured quantities of fluids. In some cases, the devices and method embodiments for such occlusion detection do not require significant modification of an infusion device and can be carried out with a minimum of additional components.

15 Claims, 13 Drawing Sheets

(56) References Cited

U.S. PATENT DOCUMENTS

| | | |
|---|---|---|
| 5,304,126 A | 4/1994 | Epstein et al. |
| 5,342,180 A | 8/1994 | Daoud |
| 5,423,743 A | 6/1995 | Butterfield |
| 5,429,483 A | 7/1995 | Tamari |
| 5,438,510 A | 8/1995 | Bryant et al. |
| 5,464,392 A | 11/1995 | Epstein et al. |
| 5,482,446 A | 1/1996 | Williamson et al. |
| 5,498,421 A | 3/1996 | Grinstaff et al. |
| 5,551,850 A | 9/1996 | Williamson et al. |
| 5,584,667 A | 12/1996 | Davis |
| 5,634,896 A | 6/1997 | Bryant et al. |
| 5,639,473 A | 6/1997 | Grinstaff et al. |
| 5,658,252 A | 8/1997 | Johnson |
| 5,695,473 A | 12/1997 | Olsen |
| 5,800,387 A | 9/1998 | Duffy et al. |
| 5,803,917 A | 9/1998 | Butterfield et al. |
| 5,885,614 A | 3/1999 | Hirsch |
| 5,935,106 A | 8/1999 | Olsen |
| 5,971,722 A | 10/1999 | Maget et al. |
| RE36,871 E | 9/2000 | Epstein et al. |
| 6,120,460 A | 9/2000 | Abreu |
| 6,158,965 A | 12/2000 | Butterfield et al. |
| 6,210,361 B1 | 4/2001 | Kamen et al. |
| 6,280,408 B1 | 8/2001 | Sipin |
| 6,302,653 B1 | 10/2001 | Bryant et al. |
| 6,310,270 B1 | 10/2001 | Huang et al. |
| 6,358,225 B1 | 3/2002 | Butterfield |
| 6,371,732 B1 | 4/2002 | Moubayed et al. |
| 6,381,493 B1 | 4/2002 | Stadler et al. |
| 6,382,923 B1 | 5/2002 | Gray |
| 6,398,760 B1 | 6/2002 | Danby |
| 6,416,291 B1 | 7/2002 | Butterfield et al. |
| 6,416,293 B1 | 7/2002 | Bouchard et al. |
| 6,447,443 B1 | 9/2002 | Keogh et al. |
| 6,447,522 B2 | 9/2002 | Gambale et al. |
| 6,464,667 B1 | 10/2002 | Kamen et al. |
| 6,471,689 B1 | 10/2002 | Joseph et al. |
| 6,475,180 B2 | 11/2002 | Peterson et al. |
| 6,485,263 B1 | 11/2002 | Bryant et al. |
| 6,485,461 B1 | 11/2002 | Mason et al. |
| 6,537,268 B1 | 3/2003 | Gibson et al. |
| 6,604,908 B1 | 8/2003 | Bryant et al. |
| 6,663,359 B2 | 12/2003 | Gray |
| 6,669,669 B2 | 12/2003 | Flaherty et al. |
| 6,740,059 B2 | 5/2004 | Flaherty |
| 6,749,403 B2 | 6/2004 | Bryant et al. |
| 6,759,386 B2 | 7/2004 | Franco |
| 6,801,420 B2 | 10/2004 | Talbot et al. |
| 6,804,002 B2 | 10/2004 | Fine et al. |
| 6,877,713 B1 | 4/2005 | Gray et al. |
| 6,905,479 B1 | 6/2005 | Bouchard et al. |
| 6,948,918 B2 | 9/2005 | Hansen |
| 6,997,202 B2 | 2/2006 | Olander |
| 7,011,682 B2 | 3/2006 | Lashinski et al. |
| 7,029,455 B2 | 4/2006 | Flaherty |
| 7,090,648 B2 | 8/2006 | Sackner et al. |
| 7,091,179 B2 | 8/2006 | Franco |
| 7,107,706 B1 | 9/2006 | Bailey, Sr. et al. |
| 7,137,964 B2 | 11/2006 | Flaherty |
| 7,150,737 B2 | 12/2006 | Purdy et al. |
| 7,153,823 B2 | 12/2006 | Franco |
| 7,163,520 B2 | 1/2007 | Bernard et al. |
| 7,166,280 B2 | 1/2007 | Franco |
| 7,187,528 B2 | 3/2007 | Talbot et al. |
| 7,193,521 B2 | 3/2007 | Moberg et al. |
| 7,264,730 B2 | 9/2007 | Connell et al. |
| 7,265,091 B2 | 9/2007 | Lue et al. |
| 7,303,680 B2 | 12/2007 | Connell et al. |
| 7,318,892 B2 | 1/2008 | Connell et al. |
| 7,338,464 B2 | 3/2008 | Blischak et al. |
| 7,351,340 B2 | 4/2008 | Connell et al. |
| 7,429,269 B2 | 9/2008 | Schwammenthal et al. |
| 7,460,350 B2 | 12/2008 | Talbot et al. |
| 7,473,239 B2 | 1/2009 | Wang et al. |
| 7,476,209 B2 | 1/2009 | Gara et al. |
| 7,503,903 B2 | 3/2009 | Carlisle et al. |
| 7,507,235 B2 | 3/2009 | Keogh et al. |
| 7,514,401 B2 | 4/2009 | Franco |
| 7,517,440 B2 | 4/2009 | Anex et al. |
| 7,534,226 B2 | 5/2009 | Mernoe et al. |
| 7,559,524 B2 | 7/2009 | Gray et al. |
| 7,604,592 B2 | 10/2009 | Freeman et al. |
| 7,621,893 B2 | 11/2009 | Moberg et al. |
| 7,654,127 B2 | 2/2010 | Krulevitch et al. |
| 7,704,227 B2 | 4/2010 | Moberg et al. |
| 7,766,301 B2 | 8/2010 | Gray et al. |
| 7,766,873 B2 | 8/2010 | Moberg et al. |
| 7,775,975 B2 | 8/2010 | Brister et al. |
| 7,776,006 B2 | 8/2010 | Childers et al. |
| 7,811,279 B2 | 10/2010 | John |
| 7,892,206 B2 | 2/2011 | Moberg et al. |
| 7,922,462 B2 | 4/2011 | Preuthun et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,944,366 B2 | 5/2011 | Krulevitch et al. |
| 7,955,295 B2 | 6/2011 | Lee et al. |
| 7,959,608 B2 | 6/2011 | Nash et al. |
| 7,963,945 B2 | 6/2011 | Miller et al. |
| 7,967,022 B2 | 6/2011 | Grant et al. |
| 7,998,111 B2 | 8/2011 | Moberg et al. |
| 8,002,747 B2 | 8/2011 | Lord et al. |
| 8,007,460 B2 | 8/2011 | Gelfand et al. |
| 8,012,121 B2 | 9/2011 | Goodson et al. |
| 8,032,226 B2 | 10/2011 | Miller et al. |
| 8,034,026 B2 | 10/2011 | Grant et al. |
| 8,062,257 B2 | 11/2011 | Moberg et al. |
| 8,065,096 B2 | 11/2011 | Moberg et al. |
| 8,100,852 B2 | 1/2012 | Moberg et al. |
| 8,105,265 B2 | 1/2012 | Demers et al. |
| 8,109,906 B2 | 2/2012 | Smisson et al. |
| 8,114,350 B1 | 2/2012 | Silver et al. |
| 8,147,511 B2 | 4/2012 | Perry et al. |
| 8,182,447 B2 | 5/2012 | Moberg et al. |
| 8,211,093 B2 | 7/2012 | Miller et al. |
| 8,223,028 B2 | 7/2012 | Mandro et al. |
| 8,267,893 B2 | 9/2012 | Moberg et al. |
| 8,282,601 B2 | 10/2012 | Mernoe et al. |
| 8,287,495 B2 | 10/2012 | Michaud et al. |
| 8,287,514 B2 | 10/2012 | Miller et al. |
| 8,298,183 B2 | 10/2012 | Menot et al. |
| 8,298,184 B2 | 10/2012 | Diperna et al. |
| 8,323,188 B2 | 12/2012 | Tran |
| 8,414,532 B2 | 4/2013 | Brandt et al. |
| 8,414,563 B2 | 4/2013 | Kamen et al. |
| 8,608,699 B2 | 12/2013 | Blomquist |
| 8,694,331 B2 | 4/2014 | DeBelser et al. |
| 2002/0040208 A1 | 4/2002 | Flaherty et al. |
| 2002/0072733 A1 | 6/2002 | Flaherty |
| 2003/0097082 A1 | 5/2003 | Purdy et al. |
| 2004/0133220 A1 | 7/2004 | Lashinski et al. |
| 2004/0138744 A1 | 7/2004 | Lashinski et al. |
| 2004/0153146 A1 | 8/2004 | Lashinski et al. |
| 2004/0260233 A1 | 12/2004 | Garibotto et al. |
| 2005/0054994 A1 | 3/2005 | Cioanta et al. |
| 2005/0060030 A1 | 3/2005 | Lashinski et al. |
| 2005/0171512 A1 | 8/2005 | Flaherty |
| 2005/0171569 A1 | 8/2005 | Girard et al. |
| 2006/0116757 A1 | 6/2006 | Lashinski et al. |
| 2006/0264835 A1 | 11/2006 | Nielsen et al. |
| 2007/0100222 A1 | 5/2007 | Mastrototaro et al. |
| 2007/0112301 A1 | 5/2007 | Preuthun et al. |
| 2007/0149926 A1 | 6/2007 | Moberg et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |
| 2008/0058697 A1 | 3/2008 | Kamen et al. |
| 2008/0082040 A1 | 4/2008 | Kubler et al. |
| 2008/0125700 A1 | 5/2008 | Moberg et al. |
| 2008/0172027 A1 | 7/2008 | Blomquist |
| 2008/0221523 A1 | 9/2008 | Moberg et al. |
| 2009/0069746 A1 | 3/2009 | Miller et al. |
| 2009/0069749 A1 | 3/2009 | Miller et al. |

(56) References Cited

U.S. PATENT DOCUMENTS

| | | |
|---|---|---|
| 2009/0069785 A1 | 3/2009 | Miller et al. |
| 2010/0037680 A1 | 2/2010 | Moberg et al. |
| 2010/0185142 A1 | 7/2010 | Kamen et al. |
| 2010/0185175 A1 | 7/2010 | Kamen et al. |
| 2010/0198183 A1 | 8/2010 | Lanigan et al. |
| 2010/0217192 A1 | 8/2010 | Moberg et al. |
| 2010/0217193 A1 | 8/2010 | Moberg et al. |
| 2011/0054397 A1 | 3/2011 | Menot et al. |
| 2011/0071465 A1 | 3/2011 | Wang et al. |
| 2011/0092894 A1 | 4/2011 | Mcgill et al. |
| 2011/0105877 A1 | 5/2011 | Wilt et al. |
| 2011/0125085 A1 | 5/2011 | Mcgill et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0160650 A1 | 6/2011 | Chong et al. |
| 2011/0160654 A1 | 6/2011 | Hanson et al. |
| 2011/0166544 A1 | 7/2011 | Verhoef et al. |
| 2011/0190694 A1 | 8/2011 | Lanier, Jr. et al. |
| 2011/0208123 A1 | 8/2011 | Gray et al. |
| 2011/0230825 A1 | 9/2011 | Kamen et al. |
| 2012/0029433 A1 | 2/2012 | Michaud et al. |
| 2012/0029708 A1 | 2/2012 | Miller et al. |
| 2012/0030610 A1 | 2/2012 | Diperna et al. |
| 2013/0012917 A1 | 1/2013 | Miller et al. |
| 2014/0039392 A1 | 2/2014 | Geipel et al. |
| 2014/0054883 A1 | 2/2014 | Lanigan et al. |
| 2014/0276409 A1 | 9/2014 | Rosinko et al. |
| 2015/0174320 A1* | 6/2015 | Grant ................ A61M 39/1011 604/535 |

FOREIGN PATENT DOCUMENTS

| | | |
|---|---|---|
| WO | WO 2005/082450 A1 | 9/2005 |
| WO | WO 2007/065944 A1 | 6/2007 |

OTHER PUBLICATIONS

US 8,333,733, 12/2012, Lanigan et al. (withdrawn)

* cited by examiner

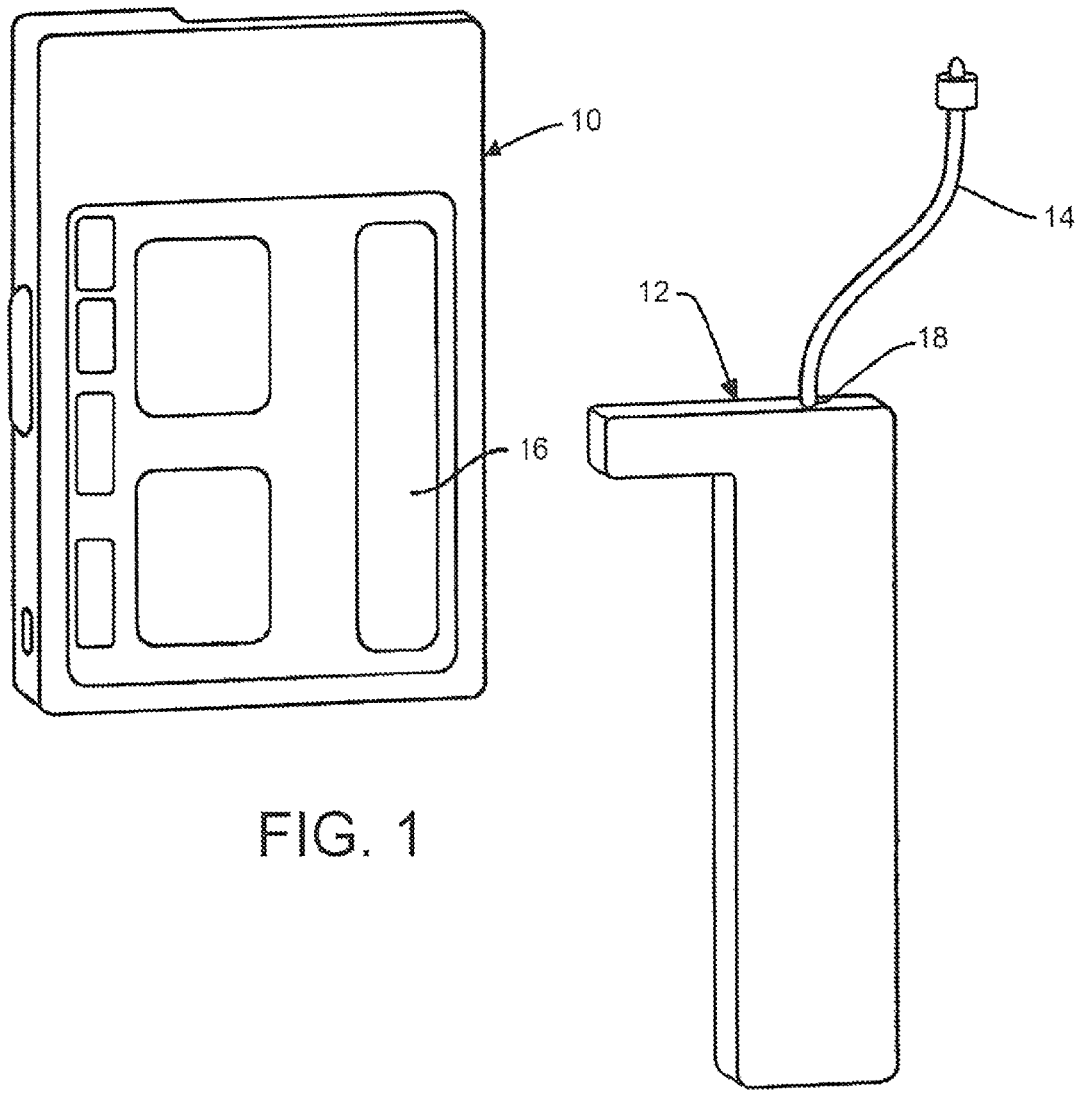

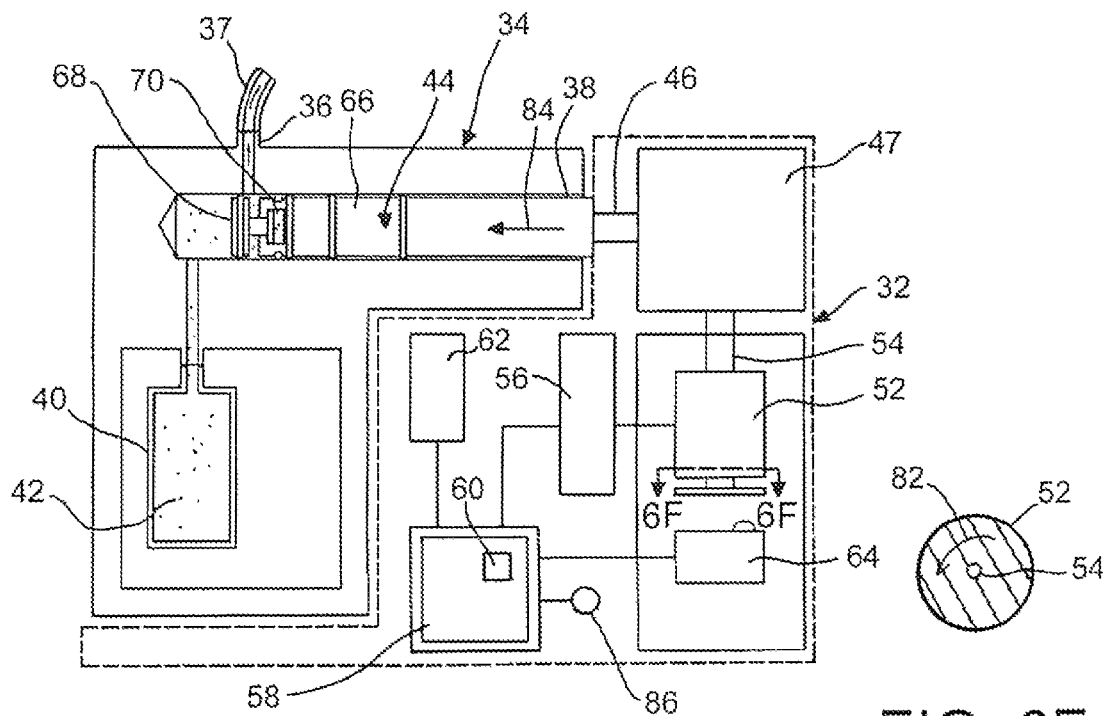
FIG. 6E
FIG. 6F
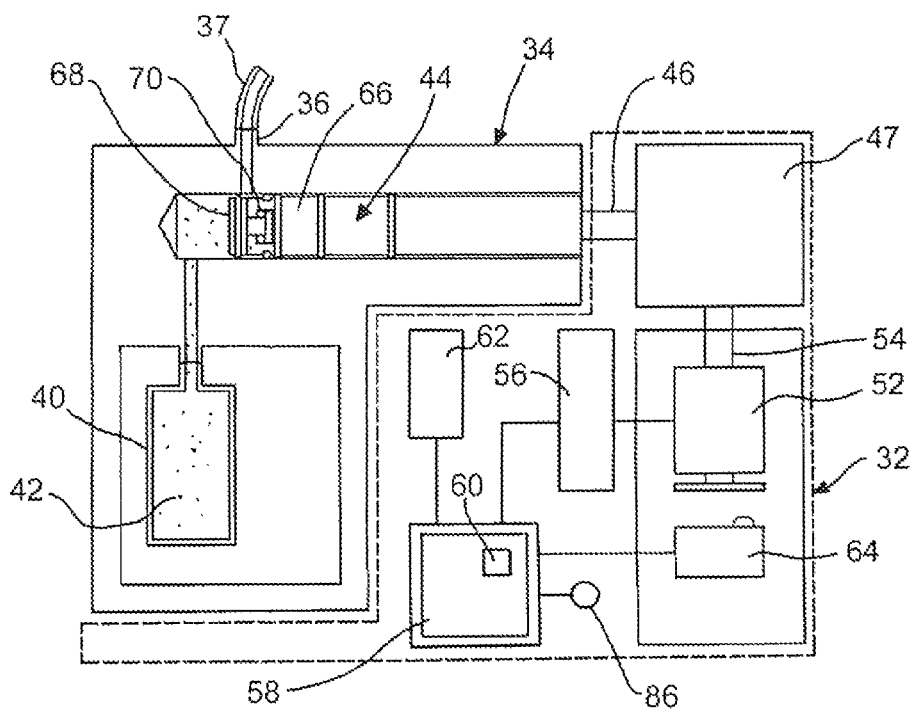
FIG. 6G

INFUSION DEVICE OCCLUSION DETECTION SYSTEM

BACKGROUND

Devices and methods that are used to deliver measured quantities of fluids may have useful applications in the industrial, academic, and medical fields. For example, in the medical industry, an infusion device may be used in order to deliver one or more therapeutic agents through an infusion set to targeted subcutaneous or intravascular regions of a patient. The ability of an infusion device to successfully deliver measured quantities of therapeutic agents to the targeted areas may be significantly hindered by an occlusion in the infusion set. Such an occlusion may result from biological or other extraneous materials which may enter the infusion set or the occlusion may result from other causes such as a kink in infusion tubing. An occlusion in an infusion set may partially or completely restrict the fluid flow through the infusion set and thereby alter the dose of therapeutic agent being delivered to a patient or prevent delivery of the therapeutic agent completely.

The ability of the infusion device to alert the user to an occlusion may therefore be important, as the user can then eliminate the occlusion and then proceed with the delivery of the therapeutic agents at the proper dose levels. What have been needed are devices and methods which are capable of detecting and alerting a user of an infusion device to a hindrance in the ability to deliver measured quantities of fluids. What have also been needed are devices and methods of occlusion detection that do not require significant modifications of or added components to an infusion device.

SUMMARY

Some embodiments are directed to a method for detecting occlusions during the use of an infusion device that may deliver therapeutic agents to a patient. The method may include generating multiple residual sum values from respective multiple variable volumes of a fluid that have been dispensed by the infusion device. The method may include performing a plurality of dispense cycles with the infusion device, each dispense cycle involving providing power to a motor that translates a spool which may be slidably disposed within a bore. The method for each dispense step may also include transferring a sub-variable volume of the fluid from a variable volume cavity disposed within the spool to an output port which is in fluid communication with the bore. The method for a dispense step may further include terminating the power to the motor and measuring a residual displacement datum of the spool after the cessation of motion of the spool with a position measurement device. The method may further include summing the residual displacement data from each dispense cycle performed while dispensing the respective variable volume of the fluid in order to generate a respective residual sum value. The method may also include individually loading a plurality of residual sum values into a filter with a filter output being the running weighted average of residual sum values which have been loaded into the filter, thereby generating a nominal filter output value. The method may also include comparing a plurality of residual sum values generated subsequent to the generation of the nominal filter output value to the nominal filter output value in order to determine if each residual sum value exceeds the nominal filter output value by a threshold difference value. The method may also include alerting a user of the infusion device to an occlusion if a plurality of successive residual sum values surpass the nominal filter output value by the threshold difference value.

Some embodiments are directed to an infusion device that is capable of detecting occlusions while delivering therapeutic agents to a patient. The infusion device may include a motor that is capable of generating a motive force when power is provided to the motor. The infusion device may also include a bore which may contain a fluid and an output port that is in fluid communication with the bore. The infusion device may also include a spool that is coupled to the motor and that has a variable volume cavity. The spool may be slidably disposed within a bore that is in fluid communication with the output port. The spool may be capable of performing a dispense step wherein power is provided to the motor and the resulting motive force translates the spool within the bore thereby decreasing the volume of the variable volume cavity and transferring a sub-variable volume of fluid from the variable volume cavity to the output port. The infusion device may also include a position measurement device configured to measure the axial position of the spool. The position measurement device can be configured to measure a residual displacement datum at the end of a dispense cycle by measuring a difference in a position of the spool at the termination of power to the motor and a position of the spool at a cessation of the motion of the spool. The infusion device may also include a control system which is configured to analyze the residual displacement datum in order to determine if an occlusion criterion is satisfied.

Some embodiments are directed at a method for detecting occlusions during the use of an infusion device which is configured to deliver therapeutic agents to a patient. The method may include performing a dispense cycle with the infusion device. The method for the dispense cycle may include providing power to a motor of the infusion device to generate a motive force and translating a spool slidably disposed within a bore with the motive force from the motor. The method for the dispense step may also include transferring a sub-variable volume of fluid from a variable volume cavity formed by the spool into an output port which is in fluid communication with the bore as a volume of the variable volume cavity is decreased by the motion of the spool. The method may also include analyzing the residual displacement datum in order to determine if an occlusion criterion is satisfied.

Some embodiments are directed to an infusion device that is capable of detecting occlusions while delivering therapeutic agents to a patient. The infusion device may include a motor capable of generating a motive force when power is provided to the motor and a bore which may contain a fluid. The infusion device may also include an output port that is in fluid communication with the bore and a spool coupled to the motor and which is slidably disposed within the bore. The spool may have a variable volume cavity and may be capable of a dispense cycle wherein power is provided to the motor and the resulting motive force translates the spool within the bore thereby decreasing a variable volume of fluid of the variable volume cavity and transferring a sub-variable volume of fluid from the variable volume cavity to the output port. The infusion device may also include a position measurement device that is configured to measure the axial position of the spool. The position measurement device may be configured to measure a residual displacement datum at the end of a dispense cycle by measuring a difference in a position of the spool at the termination of power to the motor and a position of the spool at a cessation of the motion of the spool. The infusion device may also include a control system that is configured to sum residual displacement data from a plurality of dispense cycles that deliver a respective variable volume of fluid in order to generate a residual sum value. The control system may generate a plurality of respective residual sum values from a plurality of respective variable volumes dispensed, and may then analyze the plurality of residual sum values and indicate an occluded state if the plurality of residual sum values satisfy an occlusion criterion.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

The drawings depict embodiments of the technology and are not limiting. For clarity and ease of illustration, the drawings may not be made to scale and, in some instances, various aspects may be shown exaggerated or enlarged to facilitate an understanding of particular embodiments.

FIG. 1 is a perspective view of an infusion device embodiment having a user interface.

FIG. 2 is a perspective view of an infusion cartridge embodiment with an infusion set.

FIG. 6E depicts the infusion device of FIG. 6C with the spool performing a dispense cycle wherein a portion of the fluid contained within the variable volume cavity is delivered to the output port.

FIG. 6F is a sectional view of the motor of the infusion device of FIG. 6E depicting a motion of the motorshaft.

FIG. 6G shows the infusion device of FIG. 6E after a plurality of dispense cycles have been performed thereby transferring the full capacity contained within the variable volume cavity into the output port.

DETAILED DESCRIPTION

Figure 3:
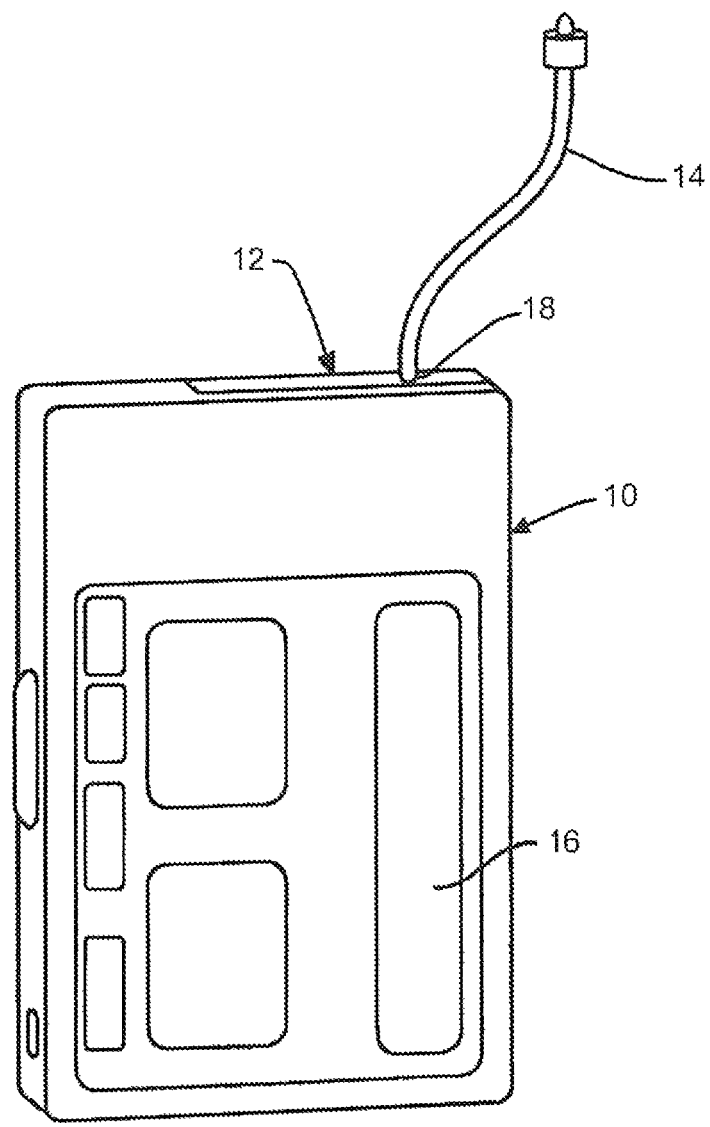
FIG. 3 depicts the infusion cartridge embodiment of FIG. 2 releasably secured to an infusion device housing of the infusion device embodiment of FIG. 1.

Some embodiments of infusion devices and the method embodiments discussed herein are directed to detection of a hindrance to the ability to deliver fluids to a patient. In some cases the hindrance may be an occlusion between an output port of the infusion device and the patient who is connected to the infusion device by an infusion set. Some embodiments may include a mechanism by which the infusion device may alert a user of the infusion device to the presence of a full or partial occlusion in the infusion set. The occlusion detection device and method embodiments discussed herein may be used in conjunction with infusion device embodiments configured to deliver a single fluid to the patient, or with infusion device configurations configured to deliver multiple fluids to the patient. Embodiments of the infusion device may also be configured with a removable infusion cartridge which can contain the fluid or fluids in a single reservoir or in multiple reservoirs respectively. The infusion cartridge may also have the capability of being refilled with the fluid or fluids by the user.

Some embodiments of an infusion device that is configured to detect a complete or partial occlusion may include a motor, a controller, a processor that is functionally linked to the controller, and a user interface which allows a user to operate the infusion device. The user interface may also provide the user with information regarding the delivery of the fluid or fluids. The infusion device may perform a dispense cycle wherein the therapeutic agent or agents are delivered to a patient through the infusion set. Each dispense cycle may be performed by a spool which may be disposed within a bore inside the infusion cartridge. The dispense cycle may begin when the processor instructs the controller to activate the motor that in turn advances the spool within the bore. As the spool is advanced in a first direction within the bore, it transfers fluid or fluids from the bore into the infusion set and subsequently to the patient.

At the termination of the dispense cycle when the controller stops the power to the motor, the spool may experience a residual displacement within the bore such that it moves in a second direction which is linearly opposed to the first direction. This is known as a "rebound" motion of the spool. It is also possible for the spool to have an "overshoot" residual displacement at the termination of a dispense cycle. In this case the spool continues to move in the first direction after the termination of power to the motor. Each residual motion and its cause will be discussed below.

For some method embodiments, data obtained by monitoring the magnitude of a residual displacement or the magnitudes of a plurality of residual displacements can be used in order to determine if an occlusion may exist between the output port of the infusion device and the patient who is connected to the infusion device by the infusion set. A position measurement device may be used in order to determine the linear position of the spool within the bore. The processor can then analyze that data to determine if the infusion set is occluded and alert the user via the user interface. The user can then clear the occlusion or replace the infusion set and then continue with the drug delivery therapy.

Figure 4A:
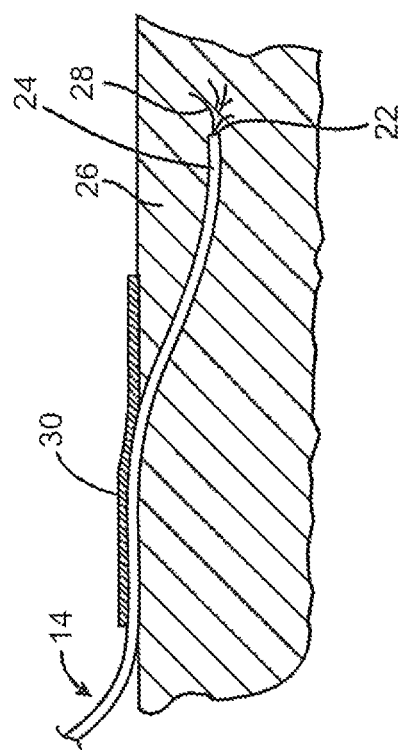
FIG. 4A is a view of the tubing of the infusion set of FIG. 4 subcutaneously positioned under the tissue of the patient.
Figure 4:
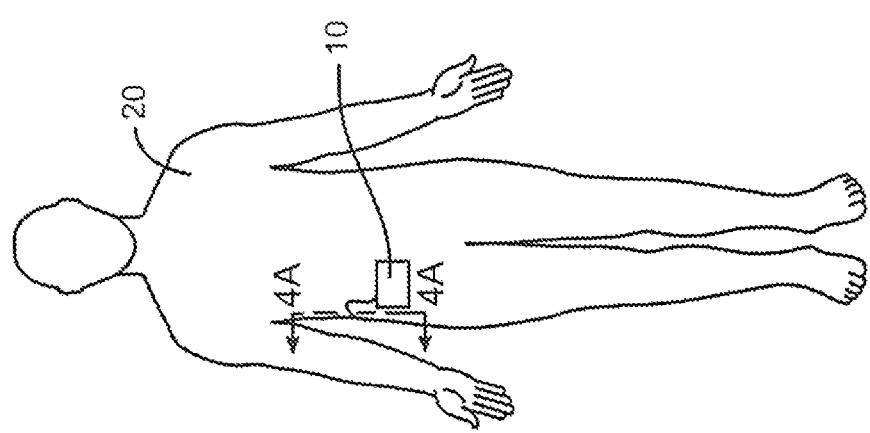
FIG. 4 depicts an infusion device attached to and in functional communication with a patient.

FIGS. 1-4A depict embodiments of an infusion device 10 with an infusion cartridge 12 having an infusion set 14, as well as a diagram of the placement of the infusion device 10 on a patient 20. An embodiment of an infusion device 10 is shown in FIG. 1. The infusion device 10 may include a user interface 16 as is shown in FIG. 1. FIG. 2 depicts an infusion cartridge 12 in fluid communication with an infusion set 14 as well as an output port 18. FIG. 3 shows the infusion cartridge 12 inserted into the infusion device 10. FIG. 4 depicts an infusion device 10 secured to the body of a patient 20. FIG. 4A is a cross sectional view of FIG. 4 showing the termination of the distal end 22 of the tubing 24 of the infusion set 14 in a subcutaneous position in the tissue 26 of the patient 20. Also shown in FIG. 4A is a fluid, including a medicament such as insulin, 28 being delivered subcutaneously into the tissue 26 of the patient 20 through the infusion set 14. The tubing 24 may be held in place on the tissue 26 with an adhesive strip 30. For some embodiments the infusion device 10 may be configured as an ambulatory infusion pump.

As has been previously discussed, it may be desirable to have the infusion device 10 alert a user to the presence of an occlusion between the output port 18 of the infusion device 10 and the patient 20, who is typically the user, and who is connected to the infusion device 10 by the infusion set 14. This is for the safety of the patient 20 and the therapeutic efficacy of the fluid 28 (typically a medicament such as insulin in the case of infusion devices used for diabetes) being delivered to the patient 20. The various components of the infusion device 10 may each play a role in the manner by which the infusion device assembly can detect and alert a user to an occlusion between the output port 18 of the infusion device 10 and the patient 20 who is connected to the infusion device 10 by the infusion set 14.

Some embodiments of the infusion device discussed herein may be configured to deliver a single fluid to the patient, while other embodiments of infusion devices may be configured to deliver multiple fluids, such as therapeutic fluids including insulin, an particularly, multiple insulin formulations of differing types, to the patient. For example, commonly owned U.S. Patent Publication No. 2013/0053816, Ser. No. 13/557,163, filed Jul. 24, 2012, by DiPerna et al. and titled Multi-Reservoir Infusion Pump Systems and Methods, is incorporated by reference herein in its entirety and discusses various embodiments of infusion devices or pumps that are configured to deliver multiple therapeutic fluids. When multiple fluids are delivered to the patient, the multiple fluids may be delivered either sequentially or simultaneously. The devices and methods of occlusion detection discussed herein may also be operatively applied to any suitable pump embodiment discussed in the incorporated patent publication 2013/0053816. Additional pump devices and methods that may be used in conjunction with the occlusion detection devices and methods discussed herein are also discussed in commonly owned U.S. Patent Publication No. 2011/0152770, Ser. No. 12/846,688, filed Jul. 29, 2010 by B. Bureson et al., titled Infusion Pump System with Disposable Cartridge Having Pressure Venting and Pressure Feedback, which is also incorporated by reference herein in its entirety. Further examples of such pumps include those disclosed in U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference. Any of the infusion devices discussed or incorporated herein may be configured to be used as ambulatory pumps which may be conveniently carried on the person of the patient during use. Examples of such commercially available ambulatory infusion devices include the T:slim® pump sold by Tandem Diabetes Care, Inc. of San Diego, Calif., the Paradigm® Revel™ pump sold by Medtronic Minimed, Inc. of Northridge, Calif. and the One Touch® Ping® pump sold by Animas Corporation of West Chester, Pa.

Although embodiments described herein may be discussed in the context of the controlled delivery of medicaments such as insulin, other indications and applications are also contemplated. Device and method embodiments discussed herein may be used for pain medication, chemotherapy, iron cleation, immunoglobulin treatment, dextrose or saline IV delivery, or any other suitable indication or application. As such, any of the infusion devices discussed or incorporated herein may be used to deliver any useful fluid, such as a therapeutic fluid or fluids, to the patient. Examples of therapeutic fluids suitable for delivery by the infusion devices discussed or incorporated herein may include antibiotics, glucose, saline, glucagon, pramlintide or any other suitable liquid medicament. Non-medical applications are also contemplated.

With regard to the treatment of diabetes, a regimented dosage of materials, in particular, the administration of insulin is typically required. In addition, the administration of insulin for a diabetic patient is one of a few medical indications wherein patient routinely administers the medicament to themselves by a subcutaneous modality. As such, providing a patient with the means to safely, reliably and comfortably administer required doses of medication may be particularly important in order to facilitate patient compliance and accurate treatment of the condition.

Blood glucose is an important factor for metabolism and the provision of energy and proper organ functioning in mammals. The accurate regulation of blood glucose is, therefore, an essential task necessary for the well-being of the mammal. For instance, the neurons of the brain of an organism depend on glucose for fueling their functioning. Hence, blood glucose levels are typically regulated by feedback loops between the brain and the pancreas. The pancreas functions in response to various hormones released by the brain by itself releasing hormones that regulate the uptake, e.g., storage, of blood sugar, or the release of stored blood sugar. For instance, two essential hormones in the regulation of blood sugar levels are insulin and glucagon, both of which are synthesized by specialized cells in the pancreas. Specifically, the β cells of the islets of Langerhans function to synthesize insulin, while the α cells of the islets of Langerhans function to synthesize glucagon.

Maintaining appropriate blood glucose homeostasis is an important factor for promoting the length and quality of life. However, there are many factors that affect the body's ability to maintain such homeostasis. For instance, factors such as the body's ability to produce or respond to insulin, one's physiological condition and/or health, the quantity and type of food one eats, one's metabolic rate, activity level, the types of activities and the exertion level in which one engages, as well as other such factors that make up a person's daily life and/or routine, all play important roles in effecting the body's ability to maintain homeostasis.

Insulin injecting pumps have been developed for the administration of insulin for those suffering from both type I and II diabetes. Insulin pumps are medical devices used for the administration of insulin in the treatment of diabetes and offer an alternative to multiple daily injections of insulin by an insulin syringe or an insulin pen. They also allow for continuous insulin therapy. There are, however, several drawbacks associated with the use of subcutaneous injection syringes and/or some currently available infusion pumps for the delivery of insulin. Patient compliance, for instance, is a major problem with respect to the use of insulin syringes. A high percent of subjects suffering from diabetes experience dread when it comes to insulin injections due to the anxiety and discomfort associated with regular use of a the needle therefore. Further complications involve the cost of the syringes, which cost may lead to the spread of infections and diseases, such as human immunodeficiency virus (HIV) and hepatitis, through the sharing and/or reusing of needles. In addition, diabetes patients who choose to use commercially available pumps to avoid the disadvantages of syringe delivery often find that wearing them together with their required infusion set tubing is uncomfortable or unwieldy, particularly while participating in sporting activities or while sleeping.

Generally a patient's insulin requirements vary greatly, as mentioned above, and may be influenced by a variety of factors (e.g., caloric intake, physiological conditions). Therefore, in some cases, it may be desirable to provide patients with a user friendly portable infusion device having an interface that facilitates its use and having features that provide useful information about the device and its functions.

Figure 5:
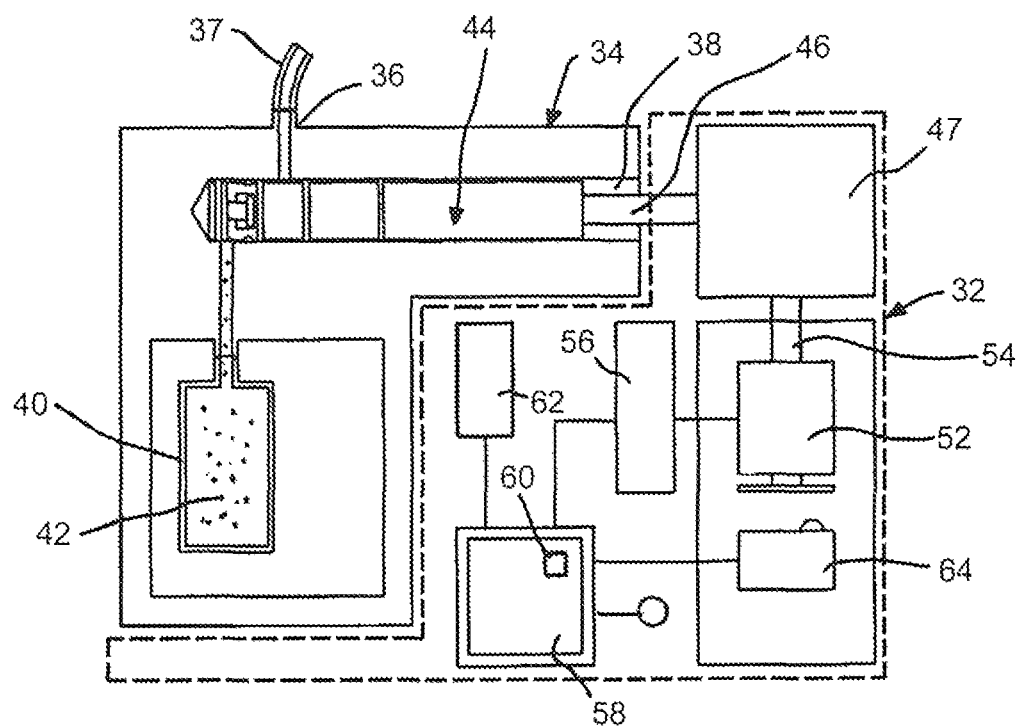
FIG. 5 is a schematic view of the infusion device of FIG. 3.

An embodiment of an infusion device 32 with the ability to detect the presence of an occlusion and that may deliver a single fluid, such as a therapeutic fluid like insulin, is shown in FIG. 5. The infusion device 32 is similar to the one shown in FIG. 3; however the infusion device 32 is shown in a schematic view in FIG. 5. The schematic view is convenient in that it allows for the visual depiction of elements that may be contained within infusion device embodiments discussed herein. The schematic view also allows for the visual depiction of the movement of elements contained within the infusion device that are necessary to discuss the sequence of events that may be used to deliver fluid and to detect the presence of an occlusion.

The infusion device 32 shown in FIG. 5 incorporates an infusion cartridge 34 which may be detached from the infusion device 32. The infusion cartridge 34 is designed such that it contains elements that may be considered disposable, which is convenient as the removable infusion cartridge 34 may be detached from the infusion device 32 and discarded once the fluid contained within it has been delivered to a patient. A new removable infusion cartridge may then be attached to the infusion device 32 in order to facilitate the delivery of more fluid to the patient. The infusion cartridge 34 may incorporate an output port 36 and a cylindrical bore 38. The output port 36 may be coupled to an infusion set 37. The infusion cartridge may also include a fluid reservoir 40 that contains a fluid 42. A cylindrical spool 44 may be slidably disposed within the bore 38. The output port 36 is in fluid communication with the bore 38, which is in turn in fluid communication with the fluid reservoir 40.

Figure 5A:
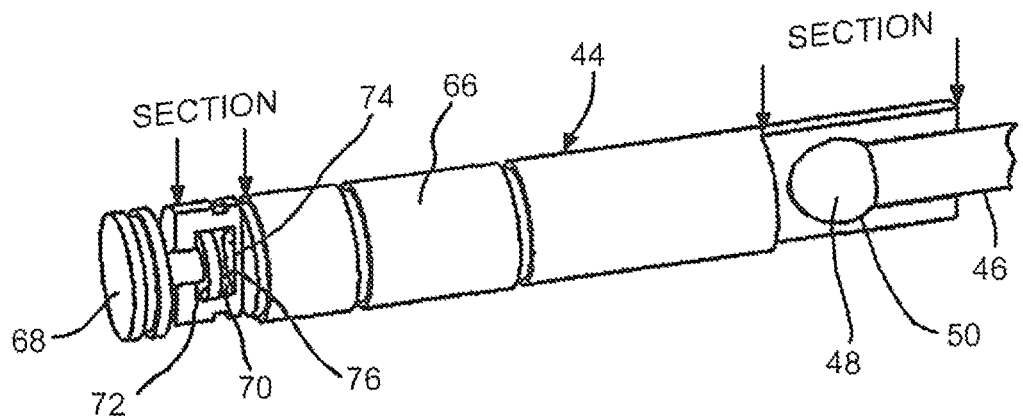
FIG. 5A is a perspective view of embodiments of a spool, a spool distal section, a variable volume cavity, and a driveshaft coupled to the spool main section.

The spool 42 disposed within the removable infusion cartridge 34 is coupled to a driveshaft 46 which is in turn coupled to a gearbox 47. When the infusion cartridge 34 is attached to the infusion device 32, a coupling element 48 of the driveshaft 46 snaps into a socket section 50 of the spool 44 as is shown in FIG. 5A thereby securing the two together. Referring to FIG. 5, the gearbox 47 is in turn coupled to a motor 52 by a motorshaft 54 which can rotate in either a first angular direction or in a second angular direction. One purpose of the gearbox 47 is to convert a rotational motion of the motorshaft 54 into a linear motion of the spool 44 within the bore 38. The motor 52 may also be in operative communication with a controller 56, which may provide power to the motor 52 such that the motorshaft 54 rotates.

FIG. 5 also depicts a processor 58 that may include a system memory 60. The system memory 60 may be used in order to store processor instructions. The processor instructions stored in the system memory 60 allow for the processor 58 to instruct other elements which are in operative communication with the processor 58 to perform specific tasks. For example the processor 58 may be in operative communication with the controller 56, and the processor instructions may instruct the processor 58 to activate the controller 56 such that it powers the motor 52 and turns the motorshaft 54. In turn, the processor instructions may instruct the processor 58 to deactivate the controller 56 such that the power to the motor 52 is terminated.

The processor 58 may also be in operative communication with a filter 62. The filter 62 may incorporate a filter input and a filter output. For some embodiments of an infusion device, the filter 62 may be an Infinite Impulse Response (IIR) filter. IIR filters are also known as exponential filters because the effects of an input change on the output decay exponentially. The IIR filter 62 may be used in order to determine the "running average" of a series of input values.

In some instances the IIR filter 62 requires the storage of only one variable, the previous filter output. The IIR filter 62 process an input and the previous filter output value according to the following equation:

$$f_\mu = (1-\alpha) \cdot r + \alpha \cdot f_{\mu-1} \qquad (1)$$

The equation averages the current filter input r with the with the previous filter output $f_{\mu-1}$ in order to determine the filter output $f^\mu$. The output may be a weighted average of the two values as determined by the filter constant α. For example if the value of α is set at 0.8, the previous filter output value $f_{\mu-1}$ is weighted at 80% and the filter input r is weighted at 20% during the averaging process.

The filter constant α may be determined by the following formula:

$$\alpha = e^{\left(\frac{-T}{\tau}\right)} \qquad (2)$$

In this formula (2) T is a time interval between specific events (for example the duration of a dispense cycle) and τ is a time constant which may be programmed into the filter at startup. The filter constant α may also be determined empirically and stored in the filter at startup.

FIG. 5 also depicts an encoder 64 that is disposed in proximity to the motor 52 and that may be in operative communication with the processor 58. For some embodiments the purpose of the encoder 64 is to relay information about the position and movement of the motorshaft 54 to the processor 58. Information about the position and movement of the motorshaft 54 may be used to indirectly measure the position spool 44 within the bore 38. In such cases, a rotational motion of the motorshaft 54 is translated into a linear motion of the spool 44 by the gearbox, 47 therefore the rotational motion of the motorshaft 54 can be correlated to a linear motion of the spool 44.

FIG. 5A depicts the spool coupled to the driveshaft 46. As shown in the figure, a spool main section 66 is coupled to a spool distal section 68. The spool distal section 68 and the spool main section 66 together form a variable volume cavity 70. The spool distal section 68 may move independently of the spool main section 66 as constrained by an enlarged portion 72 of the spool distal section 68 which is mechanically captured by a cavity 74 of the spool main section 66. Thus in such embodiments the spool distal section 68 may be displaced relative to the spool main section 66 over limited distances. Thus the volume of the variable volume cavity 70 may be determined by the position of the spool main section 66 with respect to the spool distal section 68 in such embodiments. A dispense cycle of fluid 42 may be performed by the spool 44 by decreasing the volume of the variable volume cavity 70. The maximum volume of fluid 42 that may be contained within the variable volume cavity 70 is a variable volume, defined at a point where the spool distal section 68 is displaced at a maximum separation distance from the spool main section 66 as determined by the captured enlarged portion 72 and cavity 74. FIG. 5A depicts a variable volume 76 of fluid 42 contained in the variable volume cavity 70. A dispense cycle delivers a portion of the variable volume 76 to the patient. The portion of the variable volume 76 delivered to the patient will be referred to as a sub-variable volume.

Figures 6A, 6B:
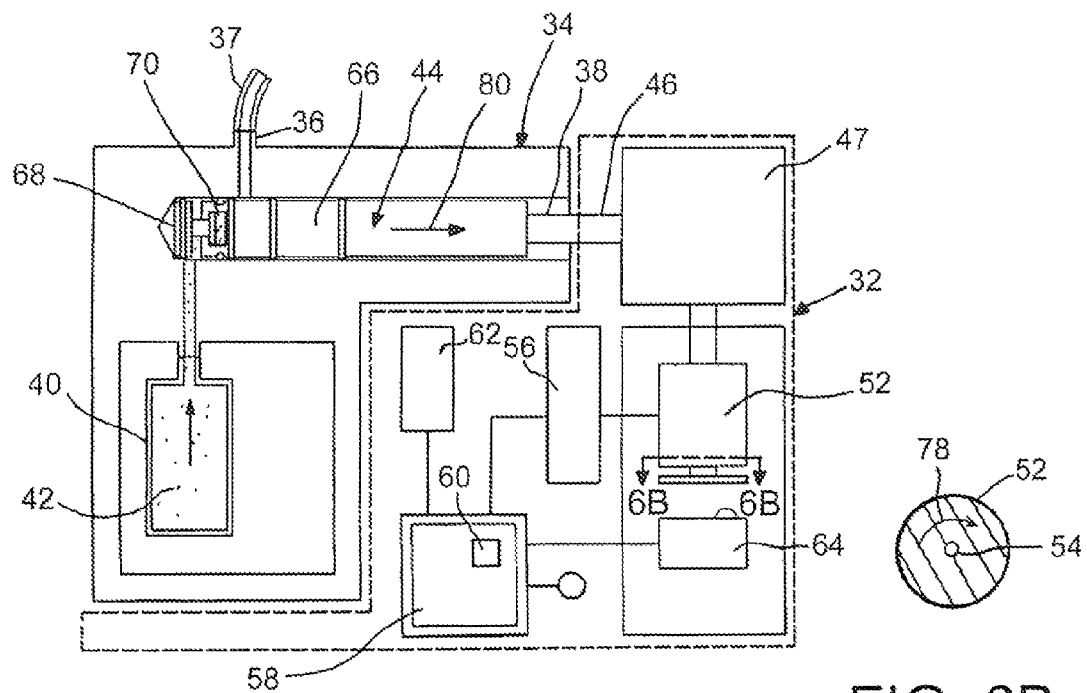
FIG. 6A is a schematic of the infusion device of FIG. 3 depicting the spool drawing a fluid from a reservoir into the variable volume.
FIG. 6B is a sectional view of a motor of the infusion device of FIG. 6A depicting an angular motion of a motorshaft.
Figures 6C, 6D:
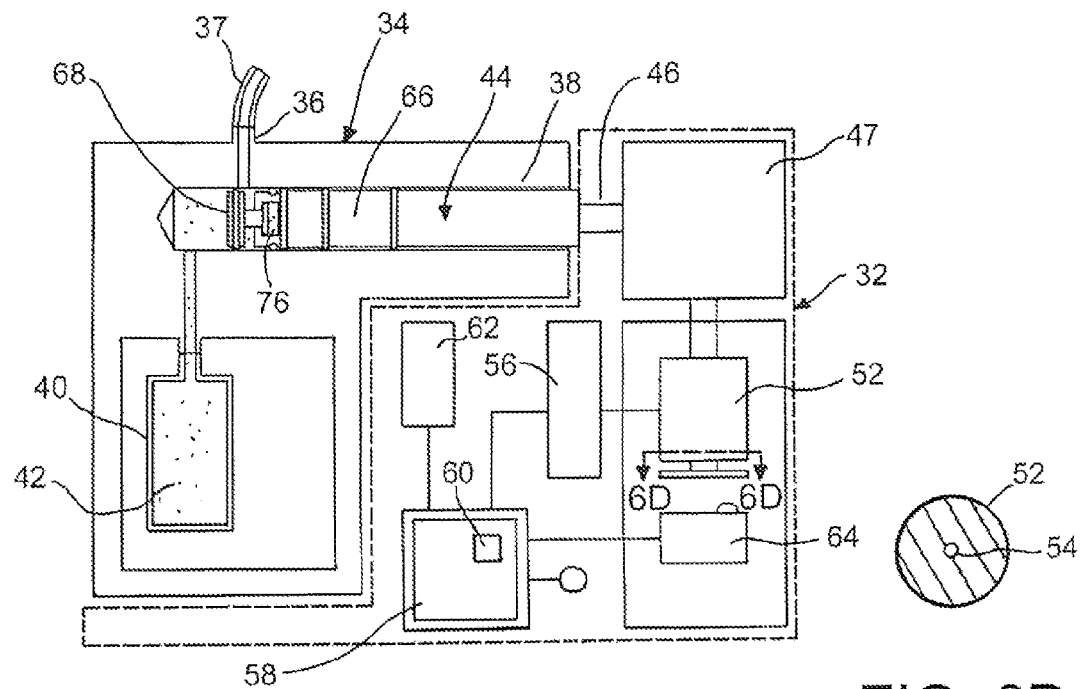
FIG. 6C depicts the infusion device of FIG. 6A with the spool moving into a position to deliver the fluid to an output port.
FIG. 6D is a sectional view of the motor of the infusion device of FIG. 6C depicting a motion of the motorshaft.

In some cases, the infusion device 32 delivers the fluid 42 contained within the fluid reservoir 40 by delivering a series of variable volumes 76 of fluid 42 until the fluid reservoir 40 is nearly empty. In turn each variable volume 76 of fluid 42 is dispensed by a series of dispense cycles, with each dispense cycle dispensing a sub-variable volume of the variable volume 76. FIG. 6A shows the infusion device 32 performing a fill step wherein the spool 44 is moved into a location to perform a dispense cycle, and the variable volume cavity 70 is filled with fluid 42 from the fluid reservoir 40. To begin a fill step, the processor 58 (using processor instructions) instructs the controller 56 to activate the motor 52 such that the motorshaft 54 rotates in a first angular direction. The rotation of the motorshaft 54 in the first angular direction is indicated by the arrow 78 shown in FIG. 6B. The gearbox 47 transforms the rotational motion of the motorshaft 54 in the first angular direction into a translational motion of the spool 44 in a first linear direction as indicated by the arrow 80 in FIG. 6A. As the spool 44 moves in the first linear direction, the encoder 64 may be used to indirectly monitor the position of the spool 44 by measuring the angular position of the motorshaft 54. The motion of the spool 44, specifically of the motion of the spool main section 66, draws fluid 42 from the fluid reservoir 40 and into the variable volume cavity 70. The fill step terminates when the variable volume cavity 76 is filled with fluid 42 and the spool distal section 68 and spool main section 66 are at maximum separation. In FIG. 6C the variable volume cavity 70 is positioned near the output port 36. At this point, the processor 58 may instruct the controller 56 to terminate power to the motor 52 as the spool 44 is in position to perform the dispense cycle.

FIGS. 6E-6G depict the infusion device embodiment 32 as it performs a dispense cycle. The dispense cycle begins with the processor 58 instructing the controller 56 to provide power to the motor 52 such that a motive force is generated. The motive force rotates the motorshaft 54 in a second angular direction as indicated by the arrow 82 in FIG. 6F. The motorshaft 54 rotating in the second angular direction activates the gearbox 47 which in turn causes the driveshaft 46 and therefore the spool 44 to translate in a second linear direction as indicated by the arrow 84 in FIG. 6E. While the spool main section 66 moves in the second linear direction, the spool distal section 68 remains motionless thereby causing closure between the spool main section 66 and spool distal section 68 and a decrease in volume of the variable volume cavity 70. As the volume of the variable volume cavity 70 is decreased, a sub-variable volume of the fluid 42 is transported from the variable volume cavity 70 to the output port 36. The processor 58 uses processor instructions to record position data from the encoder 64 in order to determine the position of the spool 44 during the dispense cycle, and the distance the spool 44 travels as measured by the encoder 64 and recorded by the processor 58 determines the duration of the dispense cycle.

Once a sub-variable volume of fluid contained within the variable volume cavity 70 has been dispensed through the output port 36, the processor 58 instructs the controller 56 to terminate power to the motor 52 thereby ceasing the powered rotation of the motorshaft 54. The spool 44 may move in either the first or second linear direction after the controller 56 terminates power to the motor 52. This movement is referred to as residual displacement of the spool 44.

The residual displacement of the spool 44 is translated through the driveshaft 46, gearbox 47, and motor 52 to the motorshaft 54 where the magnitude of the residual displacement may be measured by the encoder 64 and reported to the processor 58 as a residual displacement datum. The processor 58 may then store the residual displacement datum in the system memory 60. At this point the dispense cycle has ended in that a sub-variable volume has been delivered to the output port 36 and the processor 58 has recorded a residual displacement datum as measured by the encoder 64. It may be noted that the motion of the spool 44 depicted in FIGS. 6C and 6E carrying out a single dispense cycle is greatly exaggerated for the purpose of visualizing the dispense cycle. Practically, the motion of the spool 44 may be much less than is depicted in the two figures. That is to say, in some instances it takes multiple dispense cycles to dispense the fluid 42 contained within the variable volume cavity 70. In some cases the variable volume 76 of fluid may be dispensed in about 1 to about 100 delivery cycles. FIG. 6G shows the spool 44 after a variable volume 76 of fluid has been dispensed from the variable volume cavity 70 by multiple dispense cycles.

In some cases the infusion device elements that are used to carry out a dispense cycle may also be used in order to alert a user of the infusion device to the presence of an occlusion. If there is an occlusion in the system, the magnitude of the residual displacement data may vary over the course of multiple delivery steps. That is if there is an occlusion between the output port 36 and the patient, pressure may build up in the infusion set 37. This pressure, sometimes referred to as "back pressure", can lead to an increase in the magnitude of the residual displacement of the spool 44 after a dispense cycle. Accordingly the magnitude of the residual displacement datum as recorded by the encoder 64 may be used an indication of the presence of an occlusion.

For some embodiments, a single residual displacement datum may be analyzed in order to alert the user of the infusion device 32 to the presence of an occlusion between the output port 36 and the patient. After the dispense cycle, the encoder 64 may send the residual displacement datum to the processor 58. The processor 58 may then compare the residual displacement datum to a stored value to determine if an occlusion criterion is met. For example the processor 58 may compare the residual displacement datum to the filter output of the filter 62, and if the residual displacement datum is significantly higher than the filter output or is higher by a threshold value, the processor 58 could then trigger an alarm 86 (as shown in FIG. 6E) in order to alert a user of the infusion device to the presence of an occlusion. Alternatively the processor 58 may compare the residual displacement datum to a stored value in the system memory 60, and if the residual displacement datum is significantly higher than the stored value or is higher than a threshold value, the processor 58 could then trigger the alarm 86 in order to alert a user of the infusion device 32 to the presence of an occlusion.

As previously discussed however, the residual displacement datum may be measured either in the first linear direction (as a rebound of the spool 44) or in the second linear direction (as an overshoot of the spool 44). The ability to detect an occlusion from a single residual displacement datum may be limited by the fact that the residual displacement datum may be an overshoot value and thus may not be indicative of excess pressure in the infusion set 37.

Figure 7:
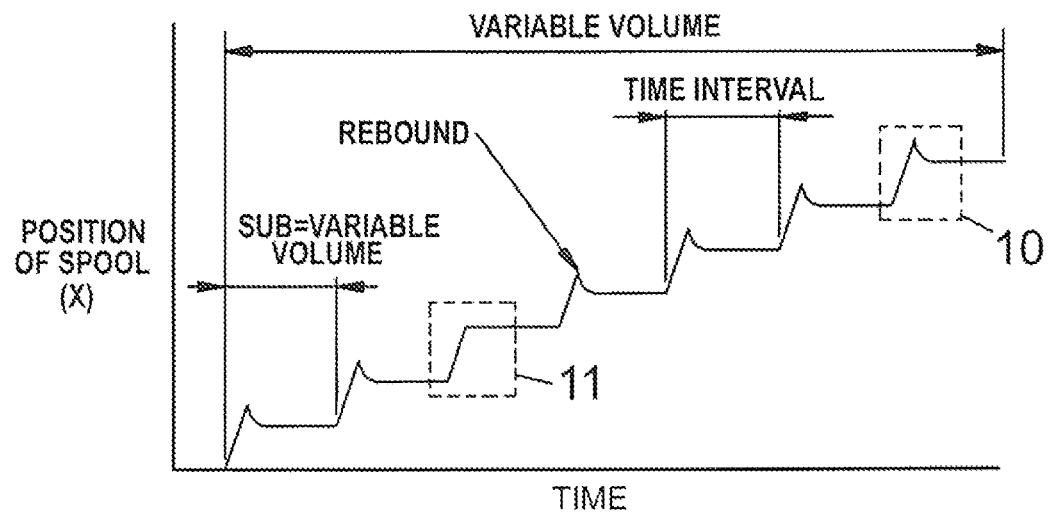
FIG. 7 is a graph that depicts the position of a spool over the time it takes to deliver a variable volume of fluid to the output port.

FIG. 7 is a graph depicting the position of the spool 44 over the course of multiple delivery steps which may deliver a variable volume 76 of fluid. The vertical axis of the chart represents the position of the spool 44 over time, which is represented as the horizontal axis of the chart. Each "step" in the chart represents one delivery cycle. The initial shape of each step determines if the residual displacement of the spool 44 is a rebound or an overshoot motion of the spool 44.

Figure 8A:
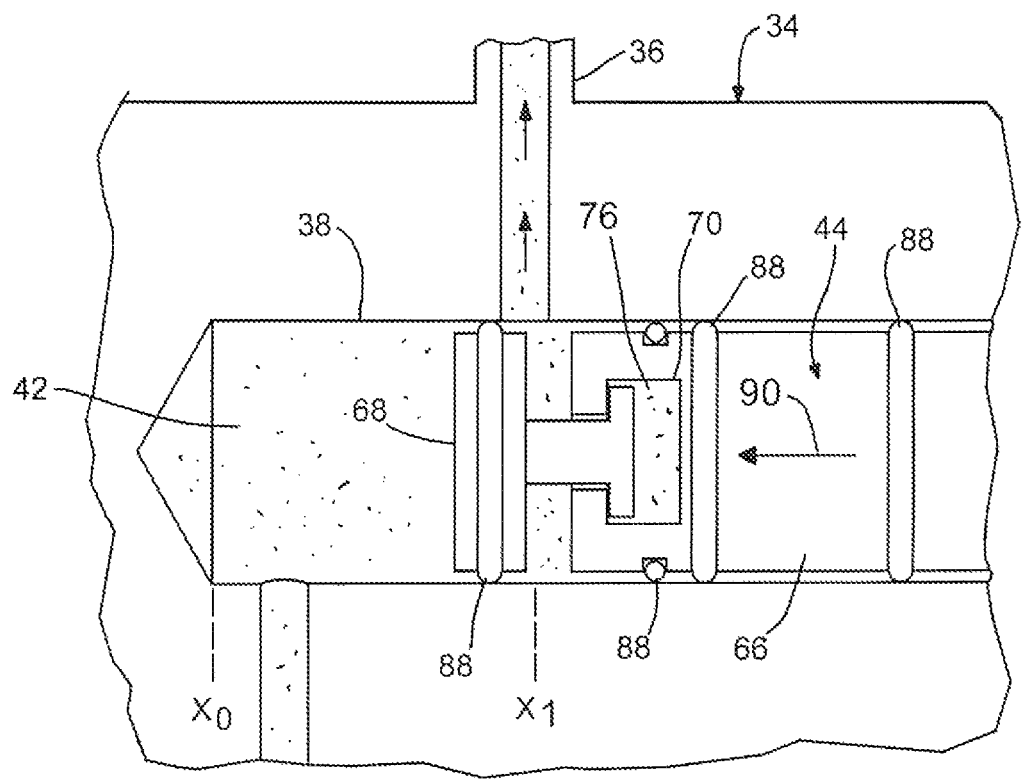
FIG. 8A is an enlarged view of the schematic of the infusion device shown in FIG. 5 depicting the spool main section of FIG. 5A at position x1 prior to a dispense cycle.
Figure 8B:
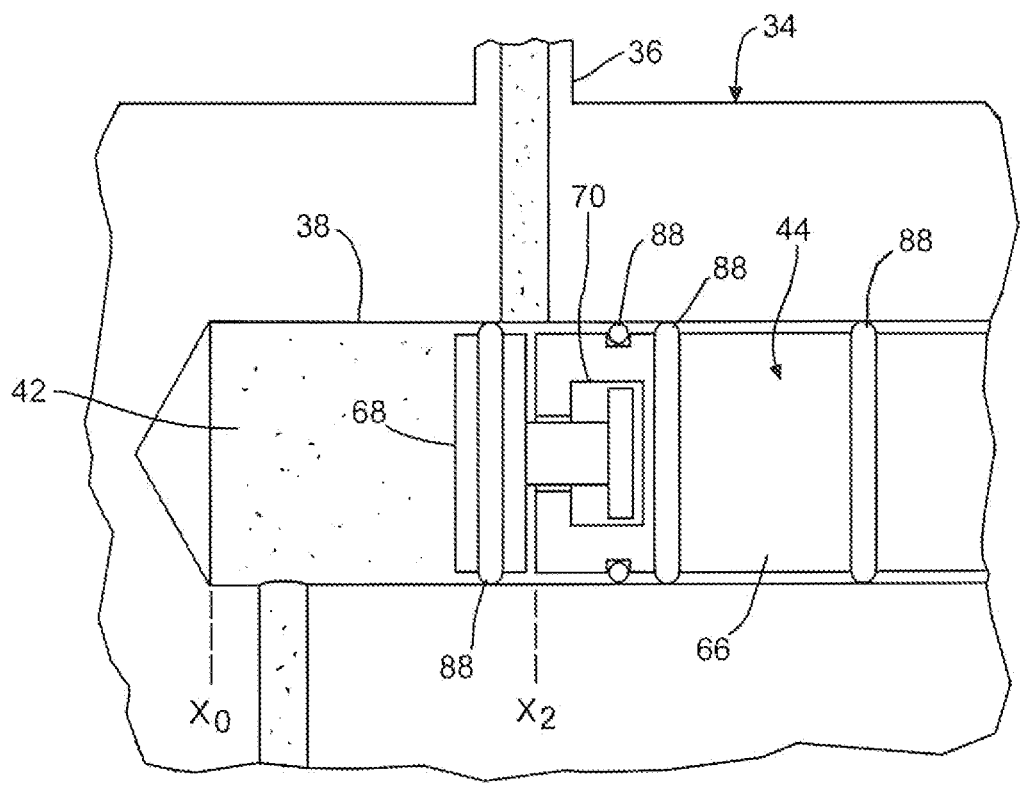
FIG. 8B depicts the spool main section of FIG. 8A at position x2 at the termination of the dispense cycle.
Figure 8C:
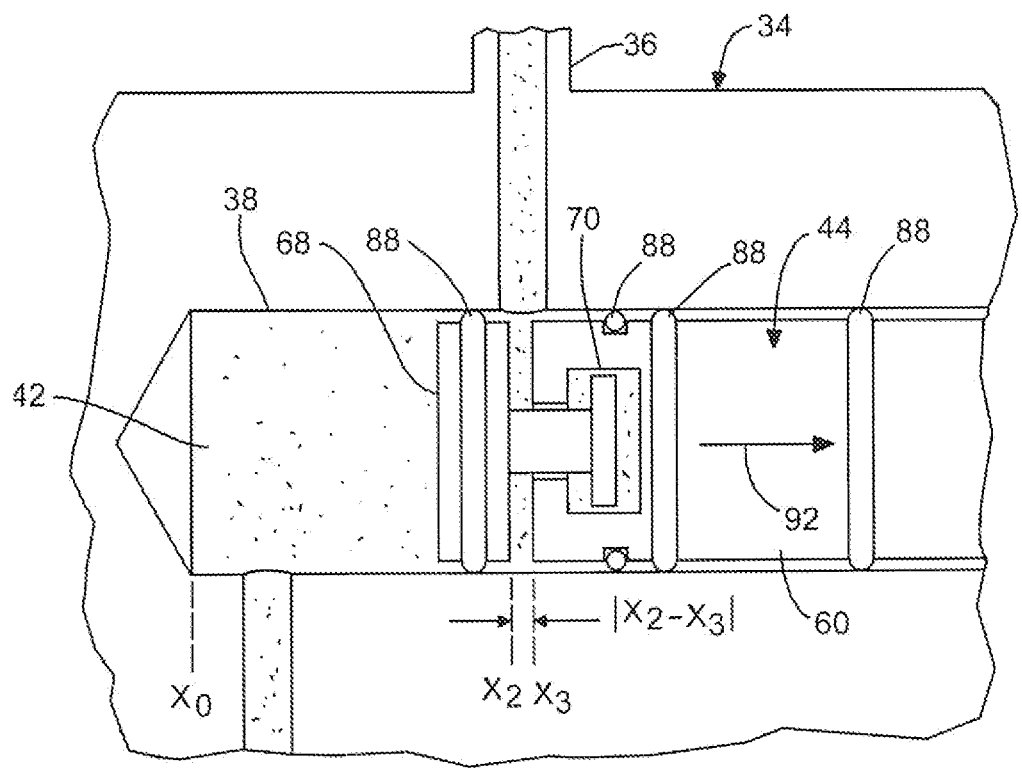
FIG. 8C shows the spool of FIG. 8B after a residual displacement has moved the spool main section to position x3 after a rebound of the spool main section.

FIGS. 8A-8C show an enlarged view of the infusion device FIG. 5, showing the spool 44, the spool main section 66, the spool distal section 68, the bore 38, the fluid 42, and the output port 36. The figures depict a single dispense cycle and subsequent residual displacement in the form of a rebound of the spool 44. The spool main section 66 is shown at position X1 (the beginning of a dispense cycle) in FIG. 8A, which also depicts a variable volume 76 of fluid 42 contained within the variable volume cavity 70. Note that in each figure the position marked as X0 indicates a relative zero position for each of the other positions. In FIG. 8A, the dispense cycle has been initiated in that the spool main section 66 has begun to move in the second linear direction as indicated by the arrow 90 and the fluid 42 is being transferred from the variable volume cavity 70 to the output port 36. FIG. 8B depicts the spool main section 66 after power to the motor 52 has been terminated. The spool main section 66 is now at position X2, and note that the spool distal section 68 has not moved from its position in FIG. 8A. FIG. 8C depicts the spool main section 66 after it has moved in the first linear direction as indicated by the arrow 92 (with the power to the motor 52 off) to position X3. The spool main section 66 has thus undergone a residual displacement in the form of a rebound. It should be noted that throughout this document and without limiting the scope of the invention, stating that a residual displacement motion of the spool 44 has occurred is equivalent to stating that a residual displacement motion of the spool main section 66 has occurred. This applies to both rebound and overshoot motion of the spool 44.

The magnitude of the rebound residual displacement may vary according to several factors. The first factor is friction between the spool main section 66 and the bore 38. For example, the spool 44 and sections thereof may be separated from the bore 38 by a plurality of flexible gaskets or seals 88 as shown in FIGS. 8A-8C. The seals 88 may become deformed as the motor 52 advances the spool main section 66 in the second linear direction. At the termination of the dispense cycle, the motor 52 is turned off and the seals 88 can recover to their original shape thereby causing the spool main section 66 to perform a residual displacement in the form of a rebound which occurs in the first linear direction. Another factor that may contribute to a rebound of the spool 44 may be fluid pressure in the infusion set 37. If a fluid lumen within the infusion set 37 is partially or completely occluded, as more fluid 42 is delivered into the fluid lumen during a delivery step, the pressure in the fluid lumen will increase. The fluid delivery step will deliver more fluid 42 into the fluid lumen and therefore the pressure in the fluid lumen will increase. This increase in pressure or backpressure from the occlusion may result in a rebound of the spool 44 within the bore 38.

Figure 9A:
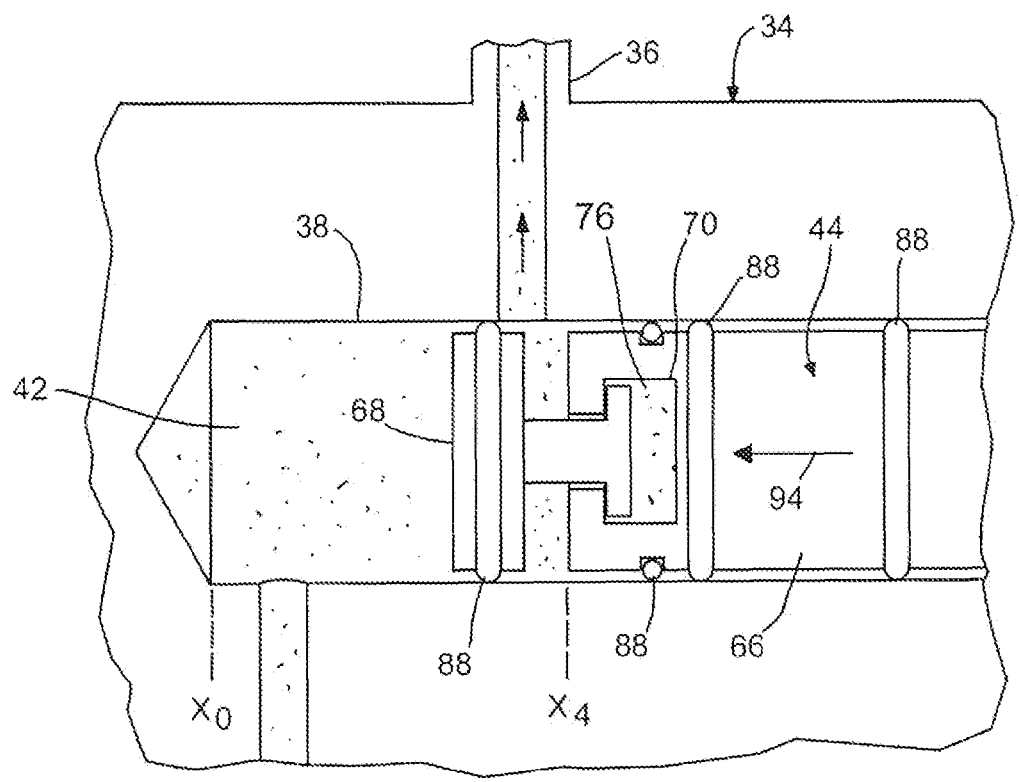
FIG. 9A is an enlarged view of the schematic of the infusion device shown in FIG. 5 depicting the spool main section at position x4 prior to a dispense cycle.
Figure 9B:
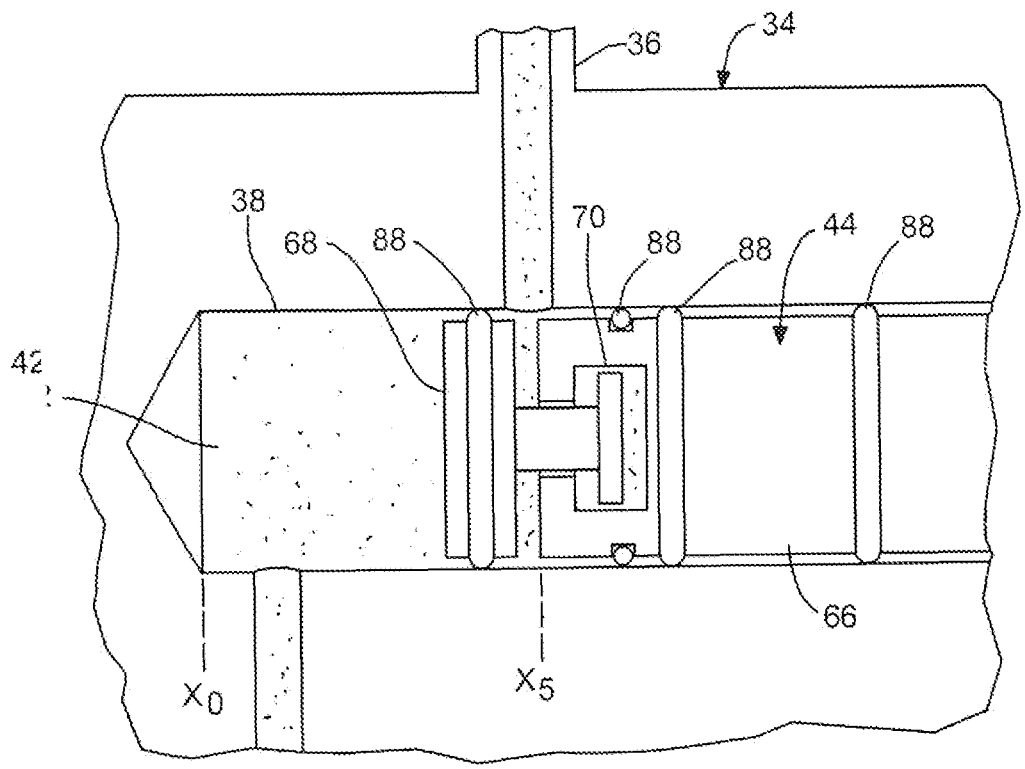
FIG. 9B depicts the spool main section of FIG. 9A at position x5 at the termination of the dispense cycle.
Figure 9C:
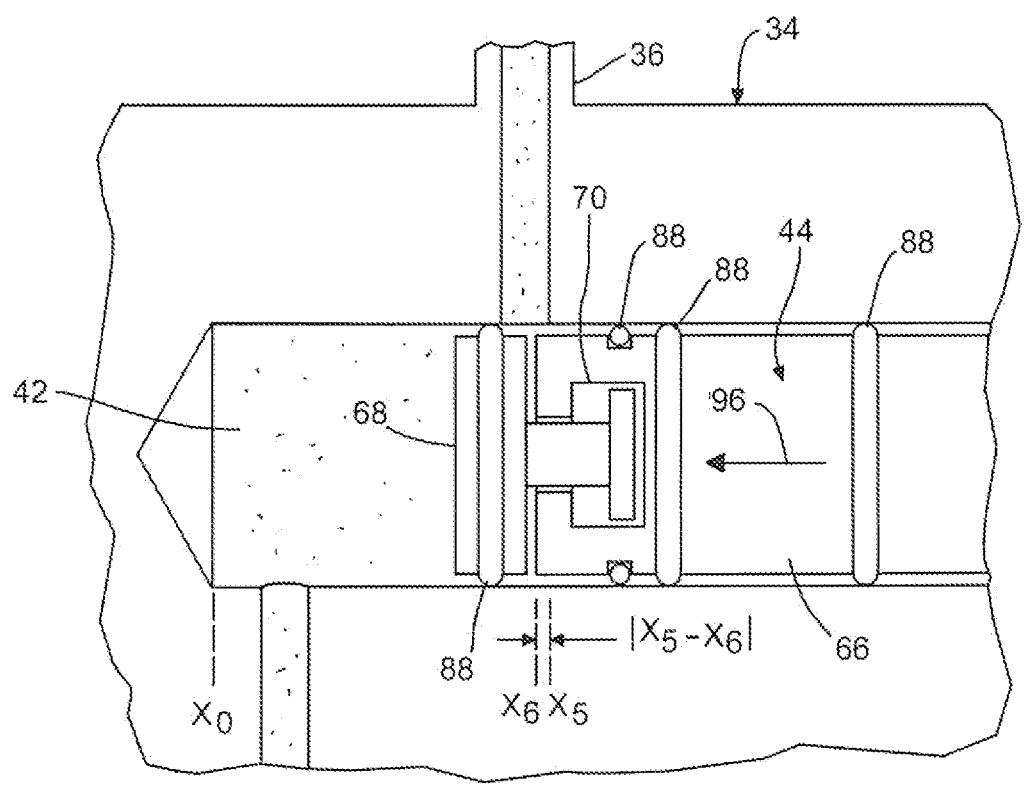
FIG. 9C depicts the spool of FIG. 9B after an overshoot residual displacement has moved the spool to position x6.

FIGS. 9A-9C are enlarged views the infusion device 32 of FIG. 5 showing the spool 44, the spool main section 66, the spool distal section 68, the bore 38, the fluid 42, and the output port 36. FIG. 9A depicts a variable volume 76 of fluid 42 contained within the variable volume cavity 70. The figures depict a single dispense cycle and subsequent residual displacement in the form of an overshoot of the spool 44 (specifically of the spool main section 66). The spool main section 66 is shown at position X4 (the beginning of a dispense cycle) in FIG. 9A. In each of FIGS. 9A-9C, the position marked as X0 indicates a relative zero position for each of the other positions. The dispense cycle has been initiated in that the spool main section 66 has begun to move in the second linear direction as indicated by the arrow 94 and the fluid 42 is being transferred from the variable volume cavity 70 to the output port 36. FIG. 9B depicts the spool main section 66 after power to the motor 52 has been terminated and the spool main section 66 is now at position X5. Note that the spool distal section 68 has not moved from the position it occupied in FIG. 9A. FIG. 9C depicts the spool main section 66 after it has moved in the second linear direction as indicated by the arrow 96 (with the power to the motor 52 off) to position X6. The spool main section 66 has thus undergone a residual displacement in the form of an overshoot.

A residual displacement in the form of an overshoot may be caused by a backlash in the system that has not yet been taken out by the motion of the spool during the dispense cycle. The backlash may be caused by friction between spool and the bore, specifically between the gaskets attached to the variable volume spool and the interior surface of the bore. The backlash may occur as the seals are deformed during the dispense cycle and then recover at the termination of the dispense cycle thereby causing an overshoot of the spool. The backlash may also be caused by spacing between the teeth of the gears disposed within in the gearbox 47.

Additionally, any significant reduction in the force to move the spool 44 may result an overshoot motion of the spool 44.

Figure 10:
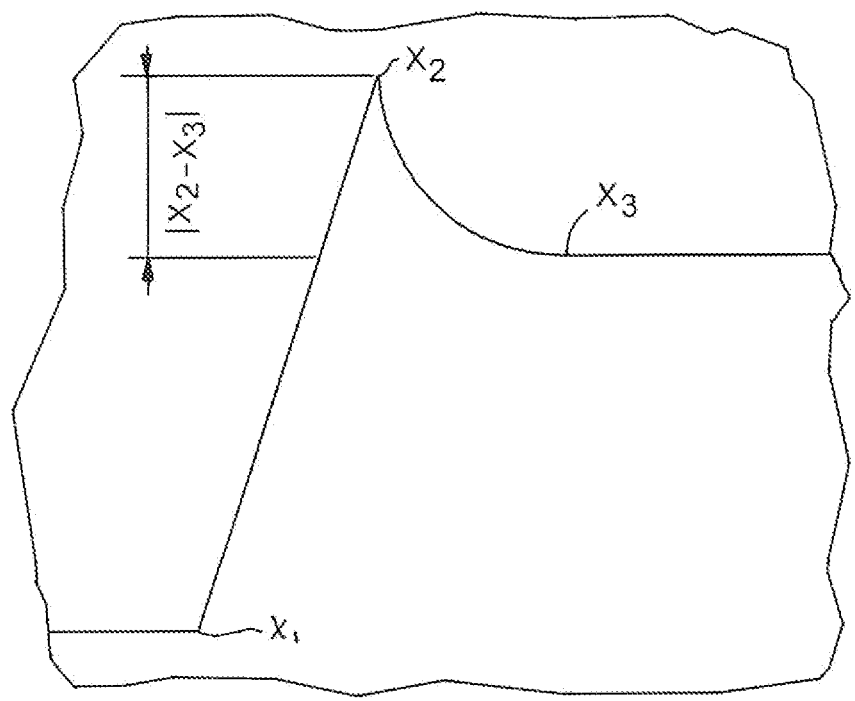
FIG. 10 is an enlarged view of the graph of FIG. 7 depicting a rebound residual displacement in the position of the spool after a dispense cycle.

FIG. 10 is an enlarged view of the chart contained in FIG. 7. FIG. 10 graphically represents the different positions of the spool main section 66 over the course of dispense cycle and a subsequent residual displacement in the form of a rebound as depicted in FIGS. 8A-8C and discussed above. Position X1 is the position of the spool main section at the beginning of the delivery cycle. Position X2 is the position of the spool main section 66 when the power to the motor 52 is terminated. Position X3 is the position of the spool main section 66 after it has undergone a residual displacement in the form of a rebound. As is indicated on the graph in FIG. 10, the residual displacement datum represents the magnitude of the difference in the position of the spool main section 66 when it is at position X2 and when it at position X3, that is the difference in the position of the spool main section 66 between the termination of power to the motor 52 and the cessation of motion of the spool main section 66.

Figure 11:
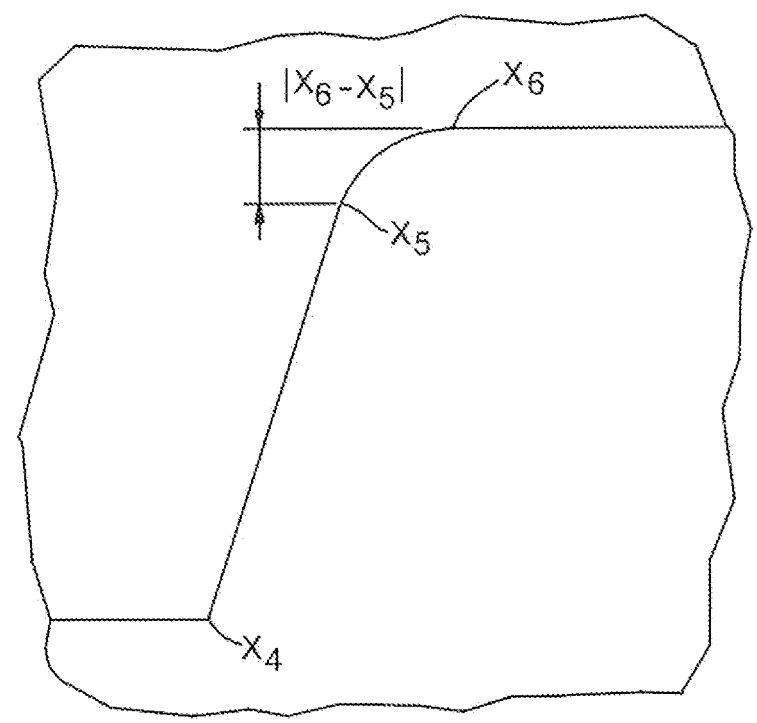
FIG. 11 is an enlarged view of the graph of FIG. 7 depicting an overshoot residual displacement in the position of the spool after a dispense cycle.

FIG. 11 is an enlarged view of a portion of the graph of FIG. 7. FIG. 10 graphically represents the different positions of the spool main section 66 over the course of the dispense cycle and subsequent residual displacement in the form of an overshoot as depicted in FIGS. 9A-9C and discussed above. Position X4 is the position of the spool main section 66 at the beginning of the delivery cycle. Position X5 is the position of the spool main section 66 when the power to the motor 52 is terminated. Position X6 is the position of the spool main section 66 after it has undergone a residual displacement in the form of an overshoot. As is indicated on the graph in FIG. 11, the residual displacement datum represents the magnitude of the difference in the position of the spool main section 66 when it is at position X5 and compared to when it at position X6. Put another way, the residual displacement datum represents the difference in the position of the spool main section 66 between the time of termination of power to the motor 52 and the time of cessation of motion of the spool main section 66.

As mentioned, because there are two types of residual displacement datum, the ability to detect an occlusion from a single residual displacement datum may be limited. If a sole residual displacement datum is recorded and it is an overshoot, this will not be indicative of excess pressure in the infusion set. Additionally, the magnitude of each individual residual displacement may be small, and therefore may be subject to various system errors. For this reason is may be advantageous to sum a plurality of residual sum data over the course of delivering a variable volume of therapeutic agent. In this manner a more statistically relevant number to be analyzed can be generated. The summing of multiple residual displacement data will be discussed referring to FIGS. 6C-6G.

The delivery of a variable volume of fluid may be broken down into a plurality of dispense cycles each of which delivers a sub-variable volume from the variable volume cavity 70 to the output port 37. Each dispense cycle may begin with the processor 58 instructing the controller 56 to provide power to the motor 52 in order to generate a motive force. The motive force causes the motorshaft 54 to rotate in the second angular direction as shown in FIG. 6F. The gearbox 47 translates the rotation of the motorshaft 54 in the second angular direction into a motion of the driveshaft 46 and spool 44 in the second linear direction indicated by the arrow in FIG. 6E. The motion of the spool 44 in the second linear direction decreases the volume of the variable volume cavity 70 formed by the spool main section 66 and the spool distal section 68 which remains motionless within the bore 38.

As the volume of the variable volume cavity 70 is decreased by the motion of the spool main section 66, the fluid 40 is transferred from the variable volume cavity 70 to the output port 36. The fluid 40 is then delivered to the patient through the infusion set 37. The processor 58 may then instruct the controller 56 to terminate power to the motor 52. Although power to the motor 52 has been terminated, the spool 44 may experience a residual displacement. The residual displacement will be translated from the spool 44 to the motorshaft 54 through gearbox 47 which transforms the linear motion of the driveshaft 46 and spool 44 into a rotational motion of the motorshaft 54. The magnitude of the residual displacement may be measured by the encoder 64, which measures the angular position of the motorshaft 54. The processor 58 which is on operative communication with the encoder 64 records a residual displacement datum and stores it in the system memory 60. The dispense cycle concludes at the cessation of motion of the spool main section 66.

Multiple dispense cycles, each of which dispenses a sub-variable volume, may be required to dispense a variable volume 76 of fluid to a patient. It is possible for the processor 58 to store in the system memory 60 each residual displacement datum measured by the encoder 64 alter each dispense cycle. After the delivery of the variable volume 76 of fluid 42, the processor 58 may sum the residual displacement data stored in the system memory 60. The processor 58 may sum the residual displacement data using an algorithm or using a summing circuit. By summing the residual displacement data from each dispense cycle the processor 58 generates a residual sum value from the residual displacement data.

Figure 12:
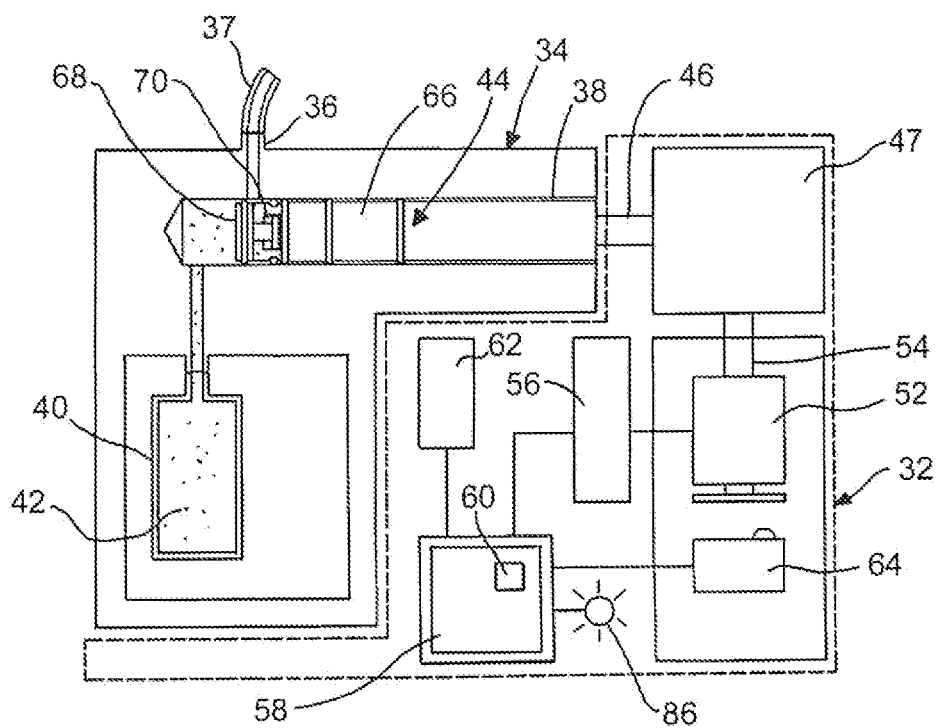
FIG. 12 depicts a schematic view of the infusion device of FIG. 5 after an alarm has been triggered.

The processor 58 may then compare the residual sum value to a stored value to determine if an occlusion criterion is met. For example the processor 58 may compare the residual sum value to a filter output of the filter 62, and if the residual sum value is higher than the filter output by a threshold value, the processor 58 could then trigger an occlusion alarm 86 (as shown in FIG. 12) in order to alert a user of the infusion device 32 to the presence of an occlusion. Alternatively, the processor 58 may compare the residual sum value to a stored value which is stored in the system memory 60, and if the residual sum is significantly higher than the stored value or higher by at least a threshold value, the processor 58 could then trigger the occlusion alarm 86 (as shown in FIG. 12) in order to alert a user of the infusion device 32 to the presence of an occlusion.

The methods and embodiments described thus far to detect an occlusion in an infusion device could be further enhanced by analyzing a plurality of residual sum values from a plurality of respective variable volumes dispensed. That is to say, if multiple respective variable volumes 76 of fluid 42 are each dispensed with multiple dispense cycles, multiple residual sum values may be generated. Each variable volume 76 will be dispensed with multiple dispense cycles, thereby resulting in a plurality of residual displacement datum for each variable volume 76 dispensed. The residual displacement data for each variable volume 76 dispensed may be summed in order to generate a respective residual sum value. The generation and analysis of multiple residual sum values allows for greater statistical accuracy with regards to detecting an occlusion than does the generation and analysis of a single residual displacement datum, or the generation and analysis of a single residual sum datum.

Again referring to FIGS. 6A-6G, the generation of multiple residual sum values begins with the dispensing of a plurality of variable volumes 76. The delivery of each variable volume 76 of fluid may in turn be broken down into a plurality of dispense cycles with each dispense cycle dispensing a sub-variable volume of fluid. Each dispense cycle may begin with the processor 58 instructing the controller 56 to provide power to the motor 52 in order to generate a motive force. The motive force causes the motorshaft 54 to rotate in the second angular direction as shown in FIG. 6E. The gearbox 47 translates the rotation of the motorshaft 54 in the second angular direction into a motion of the driveshaft 46 and spool 44 in the second linear direction indicated in FIG. 6E. The motion of the spool 44 in the second linear direction decreases the volume of the variable volume cavity 70 formed between the spool main section 66 and the spool distal section 68 which remains substantially motionless within the bore 38 during a dispense cycle.

As the volume of the variable volume cavity 70 is decreased by the motion of the spool main section 66, fluid 42 is transferred from the variable volume cavity 70 into the output port 36. The fluid 42 is then delivered to the patient through the infusion set 37. The processor 58 may then instruct the controller 56 to terminate power to the motor 52. Although power to the motor 52 has been terminated, the spool 44 may experience a residual displacement. The residual displacement will be translated from the spool 44 to the motorshaft 54 through gearbox 47 which transforms the linear motion of the driveshaft 46 and spool 44 into a rotational motion of the motorshaft 54. The magnitude of the residual displacement may be measured by the encoder 64, which may measure the angular position of the motorshaft 54. The processor 58, which is on operative communication with the encoder 64, records the residual displacement datum and stores it in the system memory 60. The dispense cycle concludes at the cessation of motion of the main spool section 66 within the bore 38.

Multiple dispense cycles with each dispense cycle dispensing a sub-variable volume are required to dispense each variable volume 76 of fluid 42 to a patient. It is possible for the processor 58 to store in the system memory 60 each residual displacement datum measured by the encoder 64 after each dispense cycle. After the delivery of each variable volume 76 of fluid 42, the processor 58 may sum the residual displacement data stored in the system memory 60 for that specific variable volume 76. The processor 58 may sum the residual displacement data for the specific variable volume 76 of fluid using an algorithm or using a summing circuit. By summing the residual displacement data for the specific variable volume 76 of fluid 42 from each dispense cycle the processor 58 may generate a residual sum value from the residual displacement data for each of the variable volumes 76 dispensed.

With the generation of multiple residual sum values, a variety of analytical methods may be applied to the residual sum data in order to determine if an occlusion may exist between the output port 36 of the infusion device 32 and a patent who is connected to the infusion device 32 an infusion set 37. For example, it may be advantageous to generate an "average" residual sum value from the initial residual sum values generated during the dispensing of multiple variable volumes 76 of therapeutic agents or fluids 42. The average residual sum values may then be used as a standard to which all residual sum values subsequently generated may be compared.

With regard to the filter 62 which has been previously described, the filter 62 has a filter output $f_\mu$ which is the weighted average (see equation 1) of the filter input r and the previous filter output $f_{\mu-1}$. The weighting between the two values may be entirely determined by the filter constant α. The filter can thus be used to create a running average of a sequential series of values; in this case, a sequential series of residual sum values. To create the average of a group of successively generated residual sum values, each residual sum value may be loaded into the filter as the filter input r (again see equation 1). The filter output $f_\mu$ will then be the weighted average of the residual sum value r just loaded into the filter, and the previous averaged residual sum value $f_{\mu-1}$. If the filter input r is the first residual sum value loaded into the filter 62, then the filter output $f_\mu$ can be that same residual sum value. The averaging will begin when the next value is loaded into the filter 62.

A plurality of residual sum values may be loaded into the filter 62 in order to generate a nominal filter output value. The nominal filter output value may be generated by loading about 2 to about 10 successive residual sum values into the filter 62. Once the nominal filter output value is generated, it may be used as a standard by which to compare residual sum values subsequently generated in order to determine if an occlusion criterion is satisfied. For example, a succession of residual sum values generated after the nominal filter output value may be compared to the nominal filter output value to determine if each residual sum value exceeds the nominal filter output value by a threshold difference value.

The threshold difference value may be defined as a residual sum value being at least about 20% higher in value than the nominal filter output value. An occlusion criterion may be further defined as having at least about 2 to about 10 residual sum values exceed the nominal filter output value by the threshold difference value.

Figure 13:
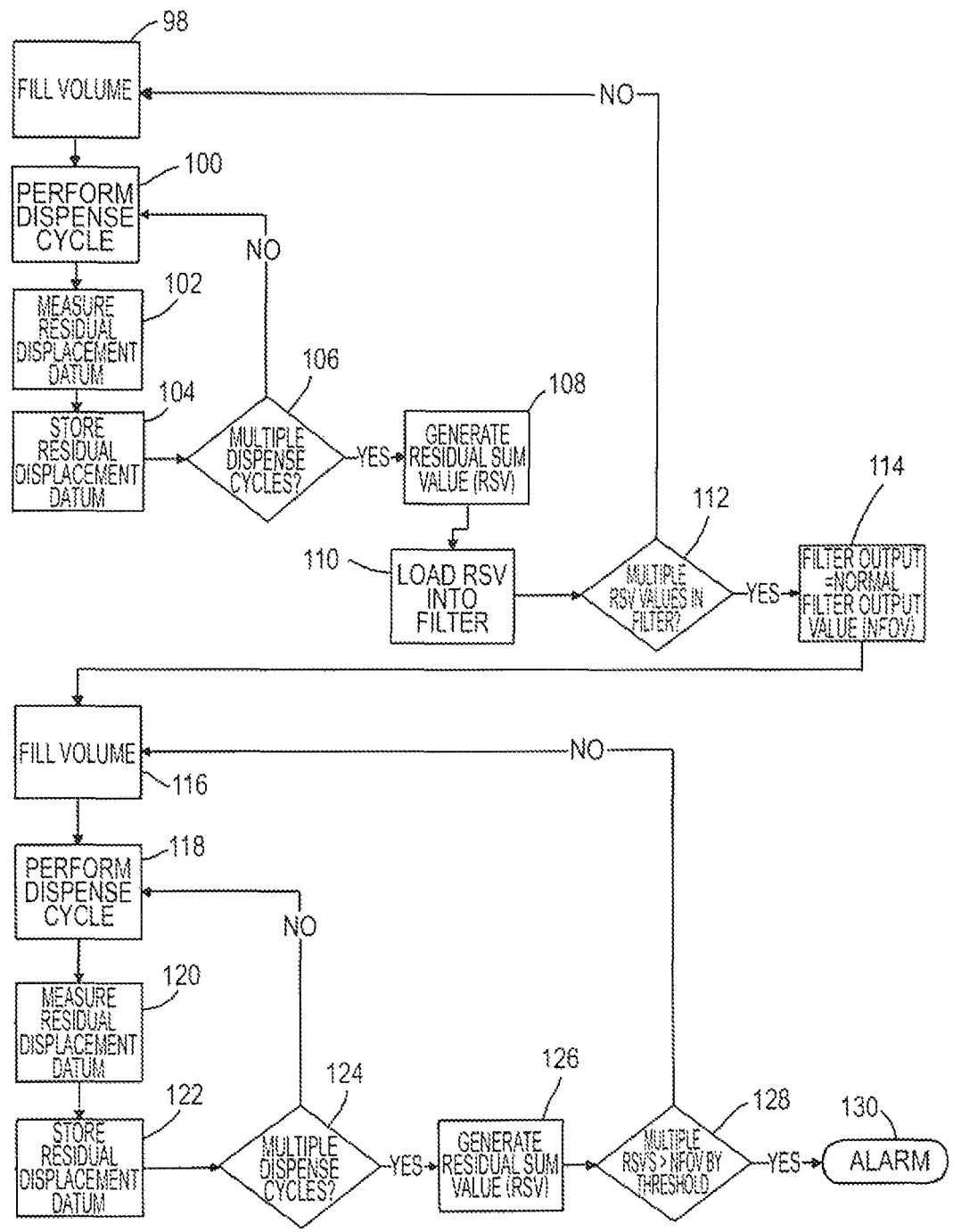
FIG. 13 is a flowchart of an embodiment of a method for detecting occlusions in an infusion device that is capable of delivering a single fluid.

FIG. 13 is a flow chart detailing the generation and analysis of multiple residual sum values in order to determine if an occlusion may exist between the output port 36 of the infusion device 32 and a patient who is attached to the infusion device 32 by the infusion set 37. The flowchart summarizes the procedure that has been discussed above for analyzing multiple residual sum values from multiple respective variable volumes 76 of fluid 42 dispensed. The flowchart in FIG. 13 begins with box 98 which depicts the variable volume cavity 70 of the spool 44 being filled with a variable volume 76 of fluid 42. Box 100 depicts the performing of a dispense cycle as described above. Box 102 depicts the measurement of a residual displacement datum by the encoder 64 after each dispense cycle. Box 104 depicts the storing of the residual displacement datum in the system memory 60 by the processor 58. Box 106 depicts multiple dispense cycles being performed until the variable volume 76 of fluid 42 is dispensed i.e. the spool main section 66 and spool distal section 68 are at maximum separation. Note that some fluid 42 will remain in the variable volume cavity 70 in this state. Box 108 depicts a residual sum value being generated by summing all of the residual displacement data which has been generated in box 102 and stored in the system memory 60 in box 104. Box 110 depicts the residual sum value generated in box 108 being loaded into the filter 62. Box 112 depicts multiple residual sum values having been loaded into the filter 62. After about 2 to about 10 residual sum values are loaded into the filter 62, the filter output is declared the nominal filter output value as depicted in box 114.

The variable volume cavity 70 is then completely filled again with a variable volume 76 of fluid 42 as depicted in box 116. Then a dispense cycle is performed as depicted in box 118. Box 120 depicts the measurement of a residual displacement datum by the encoder 64 ater each dispense cycle. Box 122 depicts the storing of the residual displacement datum in the system memory 60 by the processor 58. Box 124 depicts multiple dispense cycles being performed until the variable volume 76 of fluid 42 is dispensed i.e. the spool main section 66 and spool distal section 68 are at maximum separation. Note that some fluid 42 will remain in the variable volume cavity 70 in this state. Box 126 depicts a residual sum value being generated by summing all of the residual displacement data which has been generated in box 120 and stored in the system memory 60 in box 122. In box 128 the residual sum value is then compared to the nominal filter output value generated in box 114. The variable volume cavity 70 is then filled again and another residual sum value is generated after it is dispensed via a series of dispense cycles as depicted in boxes 116-124. The residual sum value is then compared to the nominal filter output value generated in box 114. As depicted in box 128 variable volumes 76 of fluid 42 will continue to be dispensed unless about 2 to about 10 residual sum values exceed the nominal filter output value generated in box 114 by a significant value or by a threshold difference value. When that occurs, the dispensing is stopped and an alarm is triggered as depicted in box 130.

Figure 14A:
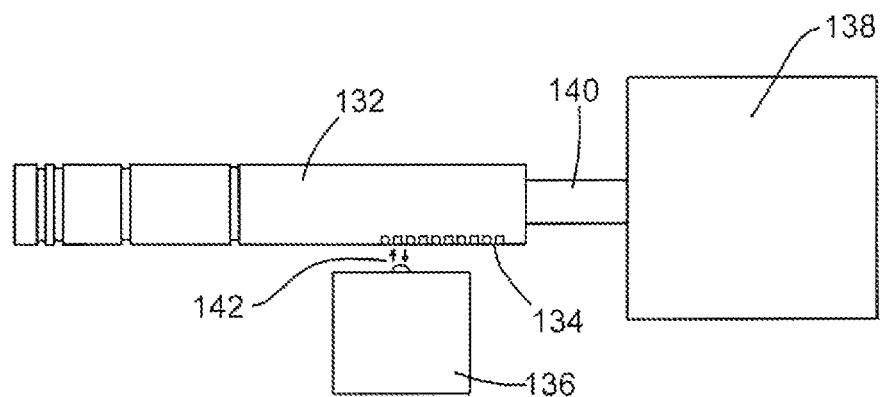
FIG. 14A depicts a gearbox, driveshaft, a spool, and a linear encoder that measures the position of the spool at a first position.
Figure 14B:
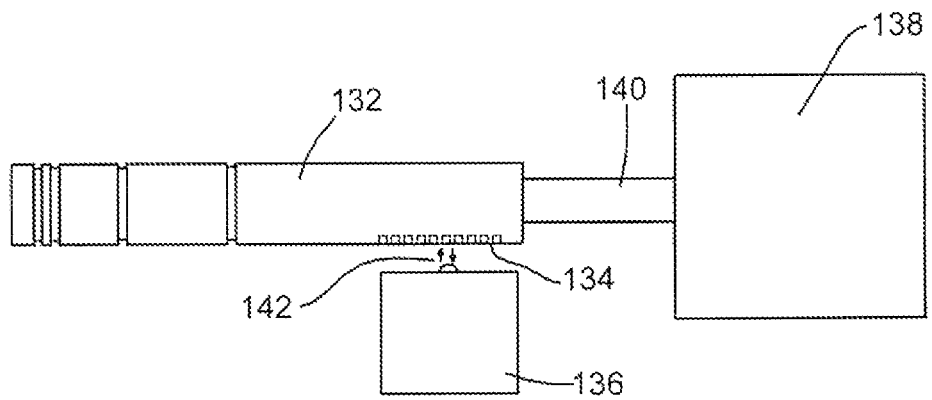
FIG. 14B depicts a gearbox, driveshaft, a spool, and a linear encoder that measures the position of the spool at a second position.

Yet another embodiment for an encoder is shown in FIGS. 14A and 14B. The encoder embodiments described thus far have had the encoder measuring the angular motion of the motorshaft. FIG. 14A depicts a spool 132 having an optical pattern 134. FIG. 14A also depicts an optical encoder 136, a gearbox 138, and a driveshaft 140. As shown in FIG. 14A, the encoder 136 sends an optical signal 142 to the optical pattern 134 thereby establishing the position of the spool 132. FIG. 14B depicts the spool 132 in a different position, with the optical encoder 136 sending an optical signal 142 to the optical pattern 134 in order to measure the new position of the spool 132. The encoder embodiment 132 depicted in FIGS. 14A and 14B therefore measures the linear position of the spool 132 directly as opposed to measuring the angular position of the motorshaft 54 as has been previously described.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology. Certain embodiments of the technology are set forth in the claim(s) that follow(s).

The invention claimed is:

1. A method for detecting occlusions during use of an infusion device, comprising:
  generating a plurality of residual sum values from a plurality of respective variable volumes dispensed from the infusion device, each variable volume being dispensed by—
    performing a plurality of dispense cycles with the infusion device, each dispense cycle comprising—
      providing power to a motor of the infusion device to generate a motive force;
      translating a spool slidably disposed within a bore with the motive force from the motor;
      transferring a sub-variable volume of fluid from a variable volume cavity of the spool into an output port which is in fluid communication with the bore as a volume of the variable volume cavity is decreased by the motion of the spool;
      terminating the power to the motor; and
      measuring a residual displacement datum of the spool while no power is provided to the motor with a position measurement device by measuring the difference in a position of the spool at the termination of the power to the motor and a position of the spool at a cessation of motion of the spool; and
    summing the residual displacement data from each dispense cycle performed while dispensing the respective variable volume of fluid in order to generate a respective residual sum value;
  individually loading a plurality of successive residual sum values into a filter with each residual sum value generating a respective filter output, the filter output being a running weighted average of residual sum values which have been loaded into the filter to generate a nominal filter output value;
  comparing a plurality of residual sum values generated subsequent to the generation of the nominal filter output value to the nominal filter output value in order to determine if each residual sum value exceeds the nominal filter output value by a threshold difference value; and alerting a user of the infusion device to an occlusion if a plurality of successive residual sum values surpass the nominal filter output value by the threshold difference value.

2. The method of claim 1, wherein each volume dispensed of the plurality of variable volumes dispensed is completely dispensed.

3. The method of claim 1, wherein dispensing a respective variable volume comprises performing about 1 dispense cycle to about 100 dispense cycles.

4. The method of claim 1, wherein the plurality of respective residual sum values that generate the nominal filter output value are generated sequentially.

5. The method of claim 1, further comprising loading about 2 to about 10 residual sum values into the filter to generate the nominal filter output value.

6. The method of claim 1, further comprising alerting a user of the device to an occlusion if about 2 to about 10 successive residual sum values are above the nominal filter output value by the threshold difference value.

7. The method of claim 1, further comprising alerting a user of the device to an occlusion if about 2 to about 10 successive residual sum values are above the nominal filter output value by a threshold difference value of at least about 20%.

8. The method of claim 1, wherein measuring a residual displacement datum comprises measuring either a rebound or overshoot displacement of the spool.

9. A method for detecting occlusions during use of an infusion device, comprising:
    performing a dispense cycle with the infusion device, the dispense cycle comprising—providing power to a motor of the infusion device to generate a motive force;
    translating a spool slidably disposed within a bore with the motive force from the motor;
    transferring a sub-variable volume of fluid from a variable volume cavity formed by the spool into an output port which is in fluid communication with the bore as a variable volume of fluid contained within the variable volume cavity is decreased by the motion of the spool;
    terminating the power to the motor; and
    measuring a residual displacement datum of the spool while no power is provided to the motor with a position measurement device by measuring the difference in a position of the spool at the termination of the power to the motor and a position of the spool at a cessation of motion of the spool; and
    analyzing, with a controller, the residual displacement datum in order to determine if an occlusion criterion is satisfied.

10. The method of claim 9, wherein analyzing the residual displacement datum in order to determine if an occlusion criterion is satisfied comprises comparing the residual displacement datum to a stored value.

11. The method of claim 9, further comprising terminating power to the motor and triggering an alarm indicating an occluded state between the output port and a patient in fluid communication with the output port if the occlusion criterion is satisfied.

12. A method for detecting occlusions during use of an infusion device, comprising:
    performing a plurality of dispense cycles with the infusion device, each dispense cycle comprising providing power to a motor of the infusion device to generate a motive force;
    translating a spool slidably disposed within a bore with the motive force from the motor;
    transferring a sub-variable volume of fluid from a variable volume cavity formed by the spool into an output port which is in fluid communication with the bore as a variable volume of fluid contained within the variable volume cavity is decreased by the motion of the spool;
    terminating the power to the motor; and
    measuring a residual displacement datum of the spool while no power is provided to the motor with a position measurement device by measuring the difference in a position of the spool at the termination of the power to the motor and a position of the spool at a cessation of motion of the spool;
    summing the residual displacement data from each dispense cycle from the same variable volume in order to generate a residual sum value; and
    analyzing, with a controller, the residual sum value in order to determine if an occlusion criterion is satisfied.

13. The method of claim 12, wherein analyzing the residual sum value in order to determine if an occlusion criterion is satisfied comprises comparing the residual sum value to a stored value.

14. The method of claim 12, further comprising terminating power to the motor and triggering an alarm indicating an occluded state between the output port and a patient in fluid communication with the output port if the occlusion criterion is satisfied.

15. The method of claim 12, wherein measuring a residual displacement datum of the spool comprises measuring either a rebound or overshoot displacement of the spool.

* * * * *